US010051359B2

(12) United States Patent
Liu et al.

(10) Patent No.: US 10,051,359 B2
(45) Date of Patent: Aug. 14, 2018

(54) METHOD OF ADJUSTING AMBIENT SOUND FOR EARPHONE, EARPHONE AND TERMINAL

(71) Applicant: Beijing Xiaoniao Tingting Technology Co., LTD., Beijing (CN)

(72) Inventors: Song Liu, Beijing (CN); Jian Zhao, Beijing (CN)

(73) Assignee: Beijing Xiaoniao Tingting Technology Co., Ltd., Beijing (CN)

( * ) Notice: Subject to any disclaimer, the term of this patent is extended or adjusted under 35 U.S.C. 154(b) by 0 days.

(21) Appl. No.: 15/393,343

(22) Filed: Dec. 29, 2016

(65) Prior Publication Data

US 2018/0192179 A1 Jul. 5, 2018

(30) Foreign Application Priority Data

Dec. 29, 2015 (CN) .......................... 2015 1 1019017

(51) Int. Cl.
*A61F 11/06* (2006.01)
*G10K 11/16* (2006.01)
(Continued)

(52) U.S. Cl.
CPC ......... *H04R 1/1041* (2013.01); *G10K 11/178* (2013.01); *G10K 11/1782* (2013.01); *H04R 1/1008* (2013.01); *H04R 1/1058* (2013.01); *G10K 2210/1081* (2013.01); *G10K 2210/3044* (2013.01)

(58) Field of Classification Search
CPC .. H04R 1/1041; H04R 1/1008; H04R 1/1058; G10K 11/1782; G10K 2210/1081; G10K 2210/3044; G10K 11/178; G10K 11/17881
USPC .... 381/71.6, 71.1, 71.7, 373, 371, 370, 182, 381/150, 122, 355, 104; 200/547, 537
See application file for complete search history.

(56) References Cited

U.S. PATENT DOCUMENTS

2006/0262938 A1* 11/2006 Gauger, Jr. ............. G10L 21/02 381/56
2010/0272279 A1 10/2010 Joho et al.
(Continued)

FOREIGN PATENT DOCUMENTS

CN 101203059 A 6/2008
CN 101401399 A 4/2009
(Continued)

OTHER PUBLICATIONS

Partial European Search Report for European Patent Application No. 16207074, dated May 17, 2017, 16 pages.
(Continued)

*Primary Examiner* — Vivian Chin
*Assistant Examiner* — Con P Tran
(74) *Attorney, Agent, or Firm* — Mintz Levin Cohn Ferris Glovsky and Popeo, P.C.; Kongsik Kim

(57) ABSTRACT

The present invention discloses a method of adjusting ambient sounds for an earphone. The earphone collects ambient sounds using at least one microphone. The method includes: determining an adjustment type and an adjustment amount for the collected ambient sounds; and adjusting, according to the determined adjustment type, the collected ambient sounds by the determined adjustment amount. The present invention also provides an earphone.

20 Claims, 8 Drawing Sheets

(51) Int. Cl.

| | |
|---|---|
| ***H03B 29/00*** | (2006.01) |
| ***H04R 1/10*** | (2006.01) |
| ***G10K 11/178*** | (2006.01) |

(56) References Cited

U.S. PATENT DOCUMENTS

2014/0348339 A1* 11/2014 Tseng .................. H04R 1/1041
381/74
2016/0300562 A1* 10/2016 Goldstein .......... G10K 11/1784

FOREIGN PATENT DOCUMENTS

CN 103269465 A 8/2013
CN 204291324 U 4/2015
CN 205454027 U 8/2016

OTHER PUBLICATIONS

Supplemental European Search Report in European Patent Application No. 16207074.2, dated Aug. 22, 2017.

* cited by examiner

METHOD OF ADJUSTING AMBIENT SOUND FOR EARPHONE, EARPHONE AND TERMINAL

CROSS REFERENCE TO RELATED APPLICATIONS

This application claims priority to Chinese Patent Application No. 201511019017.2 filed on Dec. 29, 2015, the disclosure of which is incorporated by reference herein in its entirety.

TECHNICAL FIELD

The disclosure relates to the technical field of earphones, and in particular to a method of adjusting ambient sound for an earphone, an earphone and a terminal.

BACKGROUND

The development of society informatization makes it possible to communicate at any place and at any time, and the extensive use of a variety of types of communication devices (e.g. mobile phone, Bluetooth headset, and stereo headphone) and communication technologies not only brings a lot of convenience to our life but also greatly improve our working efficiency. However, meantime it also brings about a severe problem of noises. The communication conducted in noisy environment is hard to be heard clearly and understood, and if the decibels of noises reach a certain degree, communication can not be made, and even worse, the hearing and the physical and psychological health of people are probably injured.

To deal with the problem of noises, some existing earphones are designed with a noise reduction function. These earphones denoise ambient sounds when their noise reduction function is activated and then output noise-reduced sound to the user through earphone loudspeaker(s).

However, ambient noises are variable, the energy grade and the spectrum distribution of ambient noises change with time and place, existing noise-reducing earphones only provide noise reduction activation function and noise reduction deactivation function for the user to deal with noises, such simple selection of either a noise reduction activation function or a noise reduction deactivation function makes it impossible to become user-friendly.

For example, in an environment such as an ordinary office, when the noise reduction function of an earphone is directly activated to reduce noises by more than 25 dB, the user will feel like to be in a depressing professional anechoic room, but due to the existence of ambient noises in this environment, the user cannot just turn off the noise reduction deactivation function.

SUMMARY OF THE PRESENT INVENTION

To address the problem that existing earphones with noise-reducing function are functionally monotonic in terms of noise reduction, that is to say, the noise reduction function thereof only can be either activated or deactivated, the disclosure provides a method of adjusting ambient sounds for an earphone, an earphone and a terminal.

To achieve the purposes above, the solutions of the present invention are as follows:

in accordance with an aspect of the disclosure, A method of adjusting ambient sounds for an earphone is provided, wherein the earphone is equipped externally with at least one microphone for collecting ambient sounds, and the method includes: determining an adjustment type and an adjustment amount for the collected ambient sounds; and adjusting, according to the determined adjustment type, the collected ambient sounds by the determined adjustment amount.

Optionally, a mechanically movable adjuster is arranged on the housing of the earphone or on the housing of the wire controller of the earphone, wherein the adjuster is equipped with an electrical port through which the adjuster is electronically connected with the noise reduction module and/or the monitoring module of the earphone. The step of determining an adjustment type and an adjustment amount for the collected ambient sounds may include: monitoring the movement behavior of the adjuster in real time and acquiring the movement amount and the movement type of the adjuster if the adjuster moves; determining current adjustment type for the collected ambient sounds according to the acquired movement type and determining current adjustment amount for the collected ambient sounds according to the acquired movement amount.

Optionally, the step of acquiring the movement amount and the movement type of the adjuster if the adjuster moves may include: acquiring the movement direction and the movement amount of the adjuster when the movement of the adjuster is monitored, wherein the movement amount is the amount of movement of the adjuster from the former position thereof, and the movement type is determined based on the preset correspondence between movement directions and movement types. The step of determining current adjustment type for the collected ambient sounds according to the acquired movement type and determining current adjustment amount for the collected ambient sounds according to the acquired movement amount may include: determining, based on the preset correspondence between movement types and adjustment types, the adjustment type according to the determined movement type, and acquiring current adjustment amount for the collected ambient sounds according to the preset correspondence between movement amounts and adjustment amounts.

Optionally, in a case where the movement behavior of the adjuster includes a first movement type corresponding to noise reduction adjustment and a second movement type corresponding to monitoring adjustment, the step of determining current adjustment type for the collected ambient sounds according to the acquired movement type and determining current adjustment amount for the collected ambient sounds according to the acquired movement amount may include: when monitoring that the movement behavior of the adjuster is the first movement type, determining the current adjustment type for the collected ambient sounds to be the first adjustment type for noise reduction adjustment and determining the current noise reduction amount for the collected ambient sounds according to the acquired movement amount; and/or, when monitoring that the movement behavior of the adjuster is the second movement type, determining the current adjustment type for the collected ambient sounds to be the second adjustment type for monitoring adjustment and determining the current amplification amount for the collected ambient sounds according to the acquired movement amount.

Optionally, the step of monitoring the movement behavior of the adjuster in real time and acquiring the movement amount and the movement type of the adjuster if the adjuster moves may include: setting a demarcation point on the movement track of the adjuster, determining the movement type of the adjuster to be the first movement type when detecting that the adjuster moves towards a preset side of the demarcation point whereas determining the movement type of the adjuster to be the second movement type when detecting that the adjuster moves towards the other side of the demarcation point, and acquiring the movement amount based on the displacement of the adjuster relative to the demarcation point. Optionally, the adjuster may be implemented as a rotatable component, or a pushbutton.

Optionally, the step of monitoring the movement behavior of the adjuster in real time and acquiring the movement amount and the movement type of the adjuster if the adjuster moves may include: in a case where the adjuster is implemented as a first key and a second key, determining the movement type of the adjuster to be the first movement type when monitoring that the first key is pressed whereas determining the movement type of the adjuster to be the second movement type when monitoring that the second key is pressed, and acquiring a corresponding movement amount based on the times the first or the second key is pressed.

Optionally, the step of determining current adjustment amount for the collected ambient sounds according to the acquired movement amount may include: acquiring current adjustment amount for the collected ambient sounds by looking up a correspondence table in which the preset correspondence between movement amounts and adjustment amounts is presented.

Optionally, a touchpad with a multi-point touch control function is arranged on the housing of the earphone, the touchpad is electronically connected with the main control chip of the earphone, and the noise reduction module and/or the monitoring module are/is electronically connected with or integrated in the main control chip. The step of determining an adjustment type and an adjustment amount for the collected ambient sounds may include: detecting the movement track and the movement direction of a finger of the user on the touchpad; determining an adjustment amount for the collected ambient sounds according to the detected movement track; and determining, based on the preset correspondence between movement directions and adjustment types, an adjustment type according to the detected movement direction, wherein the adjustment type for the ambient sounds collected includes a first adjustment type corresponding to noise reduction adjustment and a second adjustment type corresponding to monitoring adjustment.

Optionally, the step of determining an adjustment type and an adjustment amount for the collected ambient sounds may include: receiving, from an earphone application client installed on a terminal, an adjustment type and an adjustment amount for the collected ambient sounds, wherein the adjustment type for the collected ambient sounds includes a first adjustment type corresponding to noise reduction adjustment and a second adjustment type corresponding to monitoring adjustment.

Optionally, the method of adjusting ambient sounds for an earphone may further include: when monitoring that a mandatory monitoring mode triggering condition is met, recording the current playing volume and the current adjustment amount of ambient sounds and adjusting the collected ambient sounds by an adjustment amount of ambient sounds preset for a mandatory monitoring mode or adjusting the collected ambient sounds by an adjustment amount of ambient sounds preset for the mandatory monitoring mode and adjusting the playing volume of the earphone to a playing volume preset for the mandatory monitoring mode, whereas when monitoring that a mandatory monitoring mode triggering condition is not met, adjusting the earphone according to the recorded playing volume and the recorded adjustment amount of ambient sounds to the former working state.

Optionally, in a case where the adjuster arranged on the housing of the earphone is a touchpad with a multi-point touch control function, the mandatory monitoring mode triggering condition is whether the touchpad is covered by a palm of the user; in a case where the adjustment type and the adjustment amount are received from the earphone application client installed on a terminal, the mandatory monitoring mode triggering condition is whether the command received from the earphone application client installed on a terminal is a command of entering the mandatory monitoring mode or a command of exiting the mandatory monitoring mode exit; and in a case where a mandatory monitoring mode triggering button is arranged on the earphone, the mandatory monitoring mode triggering condition is whether the mandatory monitoring mode triggering button is pressed.

In accordance with another aspect of the disclosure, an earphone is provided which may include: at least one microphone arranged on the external side of the earphone to collect ambient sounds; an adjusting device which is adapted for the user to adjust the collected ambient sounds as needed; a main control chip which is configured to monitor the adjustment of the adjusting device and determine an adjustment type and an adjustment amount for the collected ambient sounds according to the adjustment of the adjusting device; and a noise reduction module and/or a monitoring module which are/is configured to carry out a noise reduction adjustment and/or monitoring adjustment for the collected ambient sounds by the determined adjustment amount according to the determined adjustment type.

Optionally, the adjusting device is a mechanically movable adjuster which is arranged on the housing of the earphone or on the housing of the wire controller of the earphone; the adjuster is provided with an electrical port which connects with the noise reduction module and/or the monitoring module; the noise reduction module and/or the monitoring module are/is electronically connected with or integrated in the main control chip; and the main control chip monitors the movement behavior of the adjuster in real time, and acquires the movement amount and the movement type of the adjuster if the adjuster moves, determines current adjustment type for the collected ambient sounds according to the acquired movement type and determines current adjustment amount for the collected ambient sounds according to the acquired movement amount.

Optionally, in a case where the adjuster is implemented as a rotatable component, a rotation demarcation point is set on the rotation track of the rotatable component, the main control chip determines the movement type of the rotatable component to be the first movement type when detecting that the rotatable component rotates towards a preset side of the rotation demarcation point, whereas determines the movement type of the rotatable component to be the second movement type when detecting that the rotatable component rotates towards the other side of the rotation demarcation point, and acquires the movement amount based on the rotation amount of the rotatable component relative to the rotation demarcation point; in a case where the adjuster is implemented as a pushbutton, a route demarcation point is set on a push route of the pushbutton, the main control chip determines the movement type of the adjuster to be the first movement type when detecting that the pushbutton slides towards a preset side of the route demarcation point whereas determines the movement type of the adjuster to be the second movement type when detecting that the pushbutton slides towards the other side of the route demarcation point, and acquires the movement amount based on the distance the pushbutton slides from the route demarcation point; and in a case where the adjuster is implemented as a first key and a second key, the main control chip determines the movement type of the adjuster to be the first movement type when monitoring that the first key is pressed whereas determines the movement type of the adjuster to be the second movement type when monitoring that the second key is pressed, and acquires a corresponding movement amount based on the times the first or the second key is pressed.

Optionally, in a case where the adjusting device is a mechanically movable adjuster arranged on the housing of the earphone or on the housing of the wire controller of the earphone, the adjuster is provided with an electrical port which connects with the noise reduction module and/or the monitoring module; the main control chip acquires the movement direction and the movement amount of the adjuster when detecting the movement of the adjuster, wherein the movement amount is the amount of movement of the adjuster from the former position thereof, and the movement type is determined based on the preset correspondence between movement directions and movement types; the main control chip also determines, based on the preset correspondence between movement types and adjustment types, the adjustment type according to the determined movement type, and calculates an adjustment amount for the collected ambient sounds according to the preset correspondence between movement amounts and adjustment amounts; in a case where the adjusting device is a touchpad with a multi-point touch control function which is arranged on the housing of the earphone, the touchpad is electronically connected with the main control chip of the earphone to detect the movement track and the movement direction of a finger of the user on the touchpad; the main control chip also determines an adjustment amount for the collected ambient sounds according to the detected movement track and determines, based on the preset correspondence between movement directions and adjustment types, an adjustment type according to the detected movement direction.

Optionally, the earphone according to the disclosure may further include: a mandatory monitoring mode triggering module configured to receive the triggering of a mandatory monitoring mode by the user. The main control chip is also configured to monitor, in real time, the output from the mandatory monitoring mode triggering module, determine whether or not a mandatory monitoring mode triggering condition is met according to the output from the mandatory monitoring mode triggering, and when the mandatory monitoring mode triggering condition is met, record the current playing volume and the current adjustment amount of ambient sounds and adjust the collected ambient sounds by an adjustment amount of ambient sounds preset for the mandatory monitoring mode or adjust the collected ambient sounds by an adjustment amount of ambient sounds preset for the mandatory monitoring mode and adjust the playing volume of the earphone to a playing volume preset for the mandatory monitoring mode, when the mandatory monitoring mode triggering condition is not met, adjust the earphone according to the recorded playing volume and the recorded adjustment amount of ambient sounds to the former working state.

In accordance with still another aspect of the disclosure, an earphone is provided which may include: at least one microphone arranged on the external side of the earphone to collect ambient sounds; a receiving device which is adapted to receive, from an earphone application client installed on a terminal, an adjustment type and an adjustment amount for the collected ambient sounds, wherein the adjustment type for the collected ambient sounds includes a first adjustment type for noise reduction adjustment and a second adjustment type for monitoring adjustment; a main control chip configured to determine the received adjustment type and the received adjustment amount; and a noise reduction module and/or a monitoring module configured to carry out a noise reduction adjustment and/or monitoring adjustment for the collected ambient sounds by the determined adjustment amount according to the determined adjustment type.

In accordance with yet still another aspect of the disclosure, a terminal is provided which may include: an earphone application client which is installed on the terminal to provide, on the interface thereof, a first virtual adjuster that can be touched to set an adjustment type and an adjustment amount for ambient sounds and a second virtual adjuster that can be touched to set a playing volume, wherein the adjustment type for ambient sounds includes a first adjustment type corresponding to noise reduction adjustment and a second adjustment type corresponding to monitoring adjustment; and a transmitting device configured to transmit the set adjustment type and the set adjustment amount for ambient sounds, as well as the set playing volume to the earphone.

Optionally, the first virtual adjuster and/or the second virtual adjuster may be implemented as any one of the following: virtual knobs (knob), virtual pushbuttons (pushbutton) or two virtual keys. Optionally, the first virtual adjuster and the second virtual adjuster are implemented as one virtual adjuster.

By adjusting a noise reduction amount or the volume of the monitored ambient sounds, the technical solutions provided in the present invention can solve the problems brought about by existing earphones whose noise reduction function only can be activated or deactivated and realize the flexible adjustment of ambient sounds for earphones, make earphones more functionally human-oriented and improve the performance of earphones as well as user experience.

The other features and advantages of the present invention will be more apparent with reference to the following detailed description of exemplary embodiments when read in conjunction with accompanying drawings.

BRIEF DESCRIPTION OF THE DRAWINGS

The accompanying drawings, which are incorporated in and constitute a part of the specification, illustrate embodiments of the disclosure and, together with descriptions of embodiments, set forth the principle of the disclosure.

DETAILED DESCRIPTION

Figure 1:
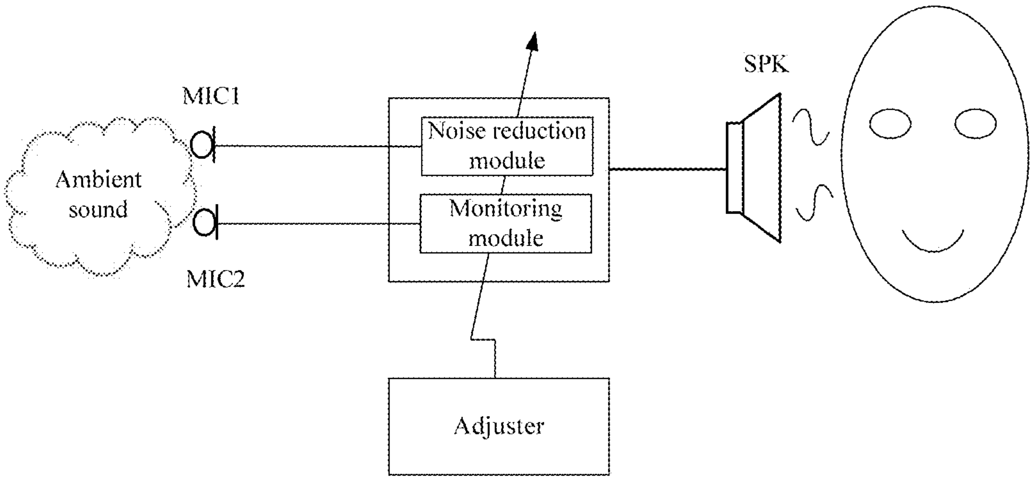
FIG. 1 is a schematic diagram illustrating one kind of application scenarios of the technical solution disclosed herein according to one embodiment of the present invention.

Various embodiments of the disclosure will be described in detail with reference to accompanying drawings. It should be noted that the relative position, order, or setting of the components or steps described herein, the reference numerals and the values involved herein, unless otherwise specified, are not to be construed as limiting the scope of the disclosure.

The following description of at least one exemplary embodiment is merely illustrative and is not intended to limit the disclosure or the application or use of the disclosure.

The technologies, methods and devices that are well known to those of ordinary skill in related arts, although not described in detail herein, should be considered as one part of the description in some cases.

Any specific numerals involved in an example of the disclosure illustrated and discussed herein are merely illustrative and are not to be construed as limitations to the disclosure. Thus, other different numerals are acceptable in other examples of the exemplary embodiments.

It should be noted that because similar reference symbols or alphabets denote similar elements in the following accompanying drawings, one reference symbol or alphabet which has been defined in one accompanying drawing will not be explained any more in the subsequent other accompanying drawings.

The disclosure provides a method of adjusting ambient sounds for an earphone, wherein the earphone collects ambient sounds through at least one microphone, and the method includes: determining an adjustment type and an adjustment amount for the collected ambient sounds; and adjusting, according to the determined adjustment type, the collected ambient sounds by the determined adjustment amount.

In the ambient sound adjustment method for an earphone, the adjustment type may include a first adjustment type for the noise reduction adjustment of the ambient sounds collected by the microphone and a second adjustment type for the monitoring adjustment of the ambient sounds collected by the microphone, however, the adjustment type is not limited herein but may include other adjustment types if needed.

In accordance with an embodiment of the disclosure, an ambient sound adjustment method for an earphone is provided. Refer to FIG. 1 which shows an application scenario of the embodiment, at least one microphone, for example, a microphone MIC1 electronically connected with a noise reduction module and a microphone MIC2 electronically connected with a monitoring module, for collecting ambient sounds is arranged on the external side of an earphone. In one variant of this embodiment, one microphone is electronically connected with a noise reduction module and a monitoring module to conduct noise reduction function and monitoring function. A mechanically movable adjuster is arranged on the housing of the earphone, wherein the mechanically movable adjuster is equipped with an electrical port through which the adjuster is electronically connected with the noise reduction module and/or the monitoring module of the earphone. The noise reduction module and the monitoring module may be integrated on the main control chip of the earphone to be realized by the single main control chip, or may be separate components from the main control chip arranged in the earphone. Here, the main control chip may be implemented as a Micro Control Unit (MCU) or a Digital Signal Processing (DSP), but not limited to these.

Figure 2:
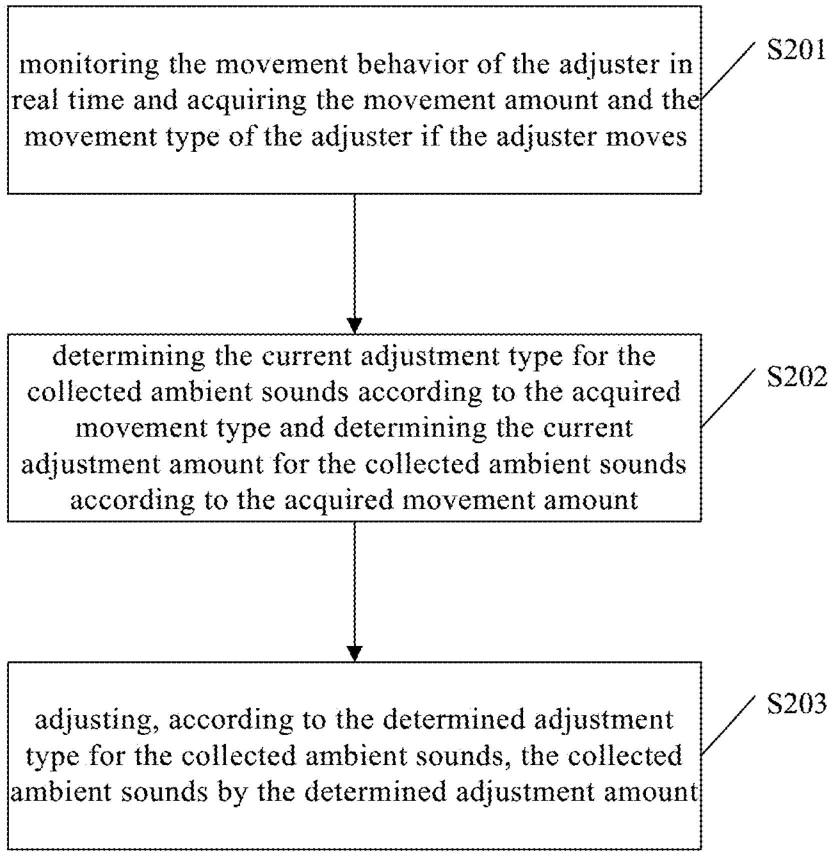
FIG. 2 is a schematic diagram illustrating a method of adjusting ambient sounds for an earphone according to one embodiment of the present invention.

In the embodiment illustrated in FIG. 2, the step of determining an adjustment type and an adjustment amount for the collected ambient sounds includes: S201: monitoring the movement behavior of the adjuster in real time and acquiring the movement amount and the movement type of the adjuster if the adjuster moves; and S202: determining current adjustment type for the collected ambient sounds according to the acquired movement type and determining current adjustment amount for the collected ambient sounds according to the acquired movement amount.

The step of adjusting, according to the adjustment type determined, the collected ambient sounds by the determined adjustment amount includes: S203: adjusting, according to the determined current adjustment type for the collected ambient sounds, the collected ambient sounds by the determined current adjustment amount.

Usually, the requirement of the user on an earphone is different in different environment, for example, in the case that the user wants to concentrate on listening to the voice output from the earphone and not to be much affected by ambient noises, the user generally uses the noise reduction mode of the earphone, that is, a mode in which the influence caused by ambient noises can be reduced. And in the case that the user wants to hear ambient sounds, for example, when communicating with people nearby, the user generally uses the monitoring mode of the earphone, that is, a mode in which the earphone can provide clear ambient sounds for the user. To be apparent, to meet different demands of users, the earphone may have other modes which are not excluded from the scope of the disclosure.

When used for communication in a noisy environment, an earphone is required to denoise ambient sounds. Noises can be reduced using a Feed-Forward (FF) noise reduction method, a Feedback (FB) noise reduction method or a hybrid FF-FB noise reduction method. At present, ambient sounds are mainly denoised in the following two ways: one way is increasing the signal-to-noise ratio of the voice signal picked up by a microphone by using an acoustic signal processing technology at the calling terminal of communication devices so that a remote-end user can hear the voice of a near-end user clearly; the other way is increasing the signal-to-noise ratio of the called terminal of communication devices so that a near-end user can hear the voice signal sent from a remote-end user clearly. Both of the two ways can be employed at the same time or one of the two ways is employed.

If the user wants to communicate with someone or monitor ambient noises without taking off the earphone, then the monitoring module in the earphone needs to be activated to amplify ambient sounds so that the user can hear ambient sounds. The monitoring function of existing earphones with a monitoring function can only be activated or deactivated, and such simple selection of either monitoring function activation or monitoring function deactivation makes it impossible to provide a good user experience.

Here, as the noise reduction function and the monitoring function are actually functionally reverse, the noise reduction module and the monitoring module involved in the disclosure may be integrated on one chip, for example, the noise reduction module and the monitoring module may be implemented by an Active Noise Control (ANC) chip or an ANC system circuit.

The embodiment also can be applied to an earphone which is only equipped with a noise reduction module or a monitoring module, in this case, the movement of the adjuster corresponds to only one movement type, for example, if the earphone is only equipped with a noise reduction module, then the movement type of the adjuster, if the adjuster moves, only corresponds to the first adjustment type corresponding to noise reduction adjustment.

According to the embodiment of the invention, a plurality of gradually varied movement amounts can be acquired from the movement of the adjuster, and different movement amounts correspond to different adjustment amounts, and thus the noise reduction amount and the volume of the monitored ambient sounds can be optionally adjusted as needed, this solves the problems brought about by existing earphones whose noise reduction function only can be either activated or deactivated, realizing the flexible ambient sound adjustment of earphones, making earphones more functionally human-oriented and improving the performance of earphones as well as user experience.

On the basis of the embodiment shown in FIG. 2, the movement behavior of the adjuster may include a first movement type corresponding to noise reduction adjustment and a second movement type corresponding to monitoring adjustment. The noise reduction adjustment is carried out by the noise reduction module, and the monitoring adjustment is carried out by the monitoring module.

In the embodiment, the movement behavior of the adjuster is classified into two types so as to achieve a noise reduction adjustment function and a monitoring adjustment function with the same adjuster. This is mainly because that noise reduction and monitoring are actually functionally reverse, the achievement of the adjustment of these two functions on the same structural component can simplify the structure of the earphone while guaranteeing the functions of the earphone available. Although the embodiment is described mainly based on the arrangement of one adjuster, the disclosure is not limited to this, for example, the invention may use two adjusters, one adjustor is arranged on the housing of one side of the earphone for noise reduction adjustment and the other adjustor is arranged on the housing of the other side of the earphone for monitoring adjustment.

In the above method embodiment of the invention, S202 may further include:

when monitoring that the movement behavior of the adjuster belongs to the first movement type, determining the first adjustment type for the noise reduction adjustment as current adjustment type for the collected ambient sounds, and determining current noise reduction amount for the collected ambient sounds collected according to the acquired movement amount; and When monitoring that the movement behavior of the adjuster belongs to the second movement type, determining the second adjustment type for monitoring adjustment as current adjustment type for the collected ambient sounds, and determining current amplification amount for the collected ambient sounds according to the acquired movement amount.

In a case where the earphone is equipped with two adjusters, the foregoing two steps may be executed selectively or at the same time according to the movements of the two adjusters.

Optionally, a correspondence table in which the correspondence between movement amounts and adjustment amounts is presented may be set in advance so that current adjustment amount for the collected ambient sounds can be acquired quickly by looking up the correspondence table using the acquired movement amount. In this way, the current adjustment amount can be acquired quickly, in no need of calculating an adjustment amount (e.g. a noise reduction amount or an amplification amount) in real time when monitoring the movement behavior of the adjuster, thus increasing the ambient sound adjustment speed of the earphone.

Further, in the embodiment shown in FIG. 2, S201 may further include: setting a demarcation point on the movement track of the adjuster, determining the movement type of the adjuster to be the first movement type when detecting that the adjuster moves towards a preset side of the demarcation point, and determining the movement type of the adjuster to be the second movement type when detecting that the adjuster moves towards the other side of the demarcation point. The movement amount can be obtained by the amount of the movement of the adjuster relative to the demarcation point.

In the above embodiment, the adjuster may be implemented as a rotatable component, or a pushbutton that can be pushed, for example, in a line, such as pushed up-and-down, or left-and-right in a line. The present invention does not limit to the type of the rotatable component or pushbutton, any type of the rotatable component or pushbutton which executes the function of the above adjuster can be used.

Further, the adjuster involved herein may be implemented in a variety of forms, and the movement behavior of the adjuster may be different when the adjuster is implemented in a different form. For example, if the adjuster is implemented as a knob, then the movement behavior of the adjuster may include two movement types: anticlockwise rotation and clockwise rotation. Moreover, the adjuster may also be implemented as a pushbutton which can be pushed up and down or as two keys. These implementation forms will be described in detail below. It should be noted that no limitations are given to the implementation form of the adjuster in the disclosure.

Figure 3:
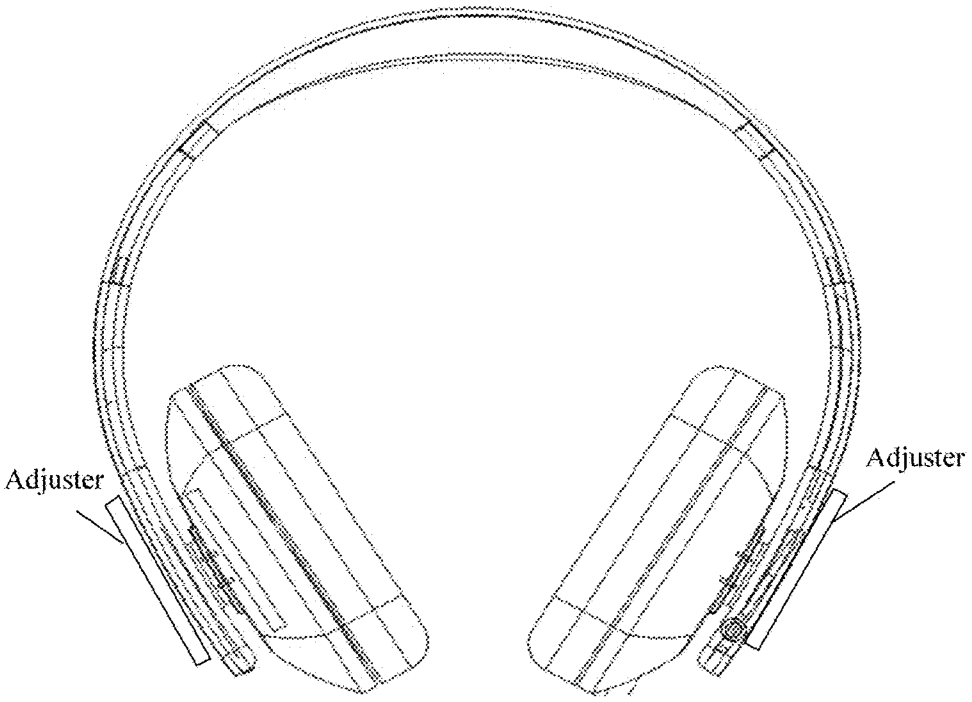
FIG. 3 is a schematic diagram illustrating one implementation form of an adjuster according to another embodiment of the present invention.

Specifically, if the adjuster is implemented as a knob, a rotation demarcation point is set on the rotation track of the adjuster, for example, the rotation demarcation point is located at a position which represents no adjustment for ambient sounds. The main control chip determines that the movement type of the knob is the first movement type corresponding to noise reduction adjustment when detecting that the knob rotates towards a preset side of the rotation demarcation point, whereas determines that the movement type of the knob is the second movement type corresponding to monitoring adjustment when detecting that the knob rotates towards the other side of the rotation demarcation point, and acquires the movement amount based on the rotation amount (or displacement) of the knob relative to the rotation demarcation point. FIG. 3 shows an implementation form of the adjuster. The adjuster, which is a knob that covers a large area of the surface of the housing of the phone receiver of a headphone, is coaxially assembled with the phone receiver of the headphone. Each phone receiver is provided with an adjuster, and each adjuster is located on the external side of the housing of the phone receiver, each adjuster adjusts ambient sounds for the phone receiver which is at the same side of the earphone as the adjuster. The size and the thickness of the knob serving as the adjuster are set so as to be held conveniently, for example, the adjuster may be a disc-shaped member with a certain thickness.

Figure 4:
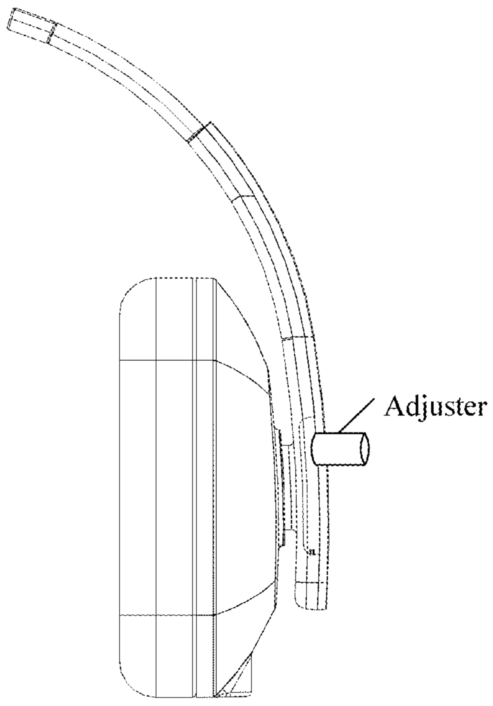
FIG. 4 is a schematic diagram illustrating another implementation form of an adjuster according to another embodiment of the present invention.

Optionally, refer to FIG. 4 which shows another implementation form of the adjuster, the adjuster is a small knob which takes the shape of a columnar member and protrudes from the external side of the housing of the phone receiver by a certain height so as to be held conveniently.

Figure 5:
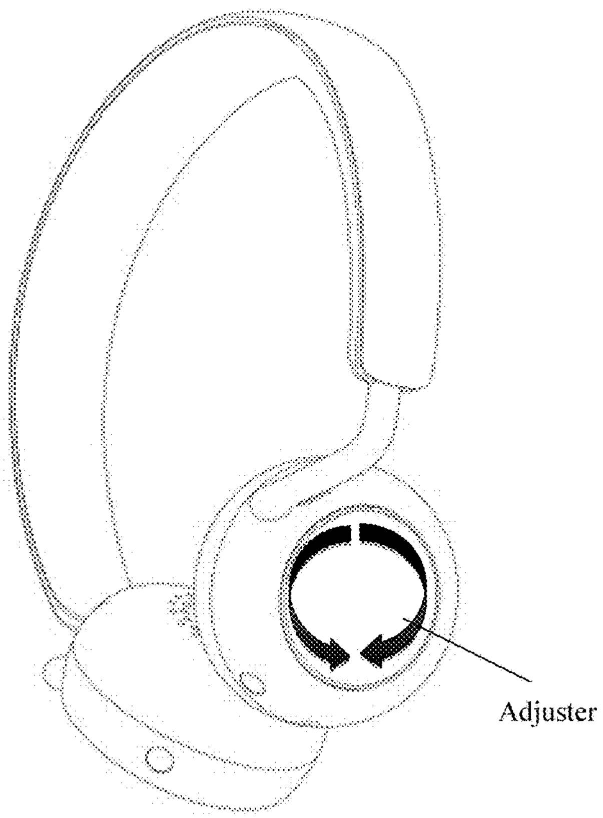
FIG. 5 is a schematic diagram illustrating still another implementation form of an adjuster according to another embodiment of the present invention.

Optionally, refer to FIG. 5 which shows still another implementation form of the adjuster, the adjuster is a rotatable panel which is arranged on the housing of the phone receiver of the earphone.

Figure 6:
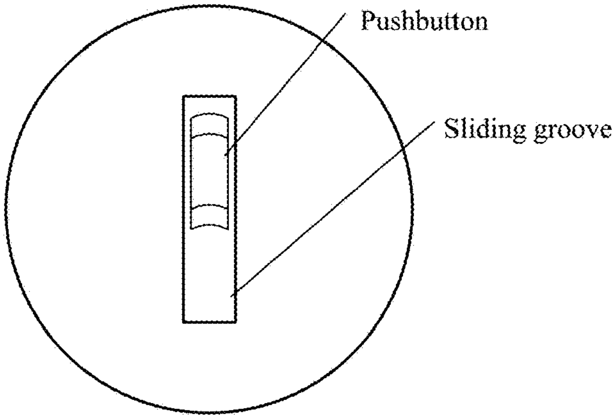
FIG. 6 is a schematic diagram illustrating yet another implementation form of an adjuster according to another embodiment of the present invention.

In the case where the adjuster is implemented as a pushbutton, a route demarcation point is set on a push route for the pushbutton, for example, the route demarcation point is located at a position which represents no adjustment for ambient sounds. It can be determined that the movement type of the pushbutton is the first movement type for noise reduction when the sliding of the pushbutton towards a preset side of the route demarcation point (the preset side is, for example, above the route demarcation point if the route demarcation point is located at the middle point of the whole push route) is detected, and it can be determined that the movement type of the pushbutton is the second movement type for monitoring adjustment when the sliding of the pushbutton towards the other side of the route demarcation point (the other side is, for example, below the route demarcation point if the route demarcation point is located at the middle point of the whole route) is detected, and the movement amount is acquired based on the distance the pushbutton slides from the route demarcation point (or the displacement of the pushbutton relative to the route demarcation point). FIG. 6 is a schematic diagram illustrating the implementation of the adjuster as a pushbutton which is installed in a sliding groove to slide up and down along the sliding groove.

Figure 7:
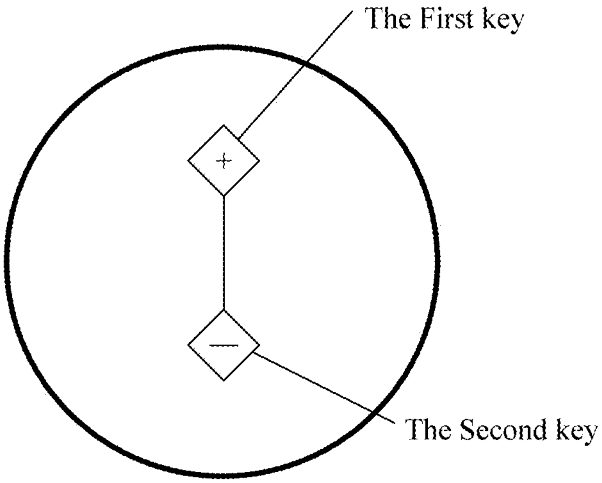
FIG. 7 is a schematic diagram illustrating yet still another implementation form of an adjuster according to another embodiment of the present invention.

Further, the adjuster may also be implemented as a first key and a second key, in this case, it can be determined that the movement type of the adjuster is the first movement type for noise reduction adjustment when a press on the first key is monitored, and it can be determined that the movement type of the adjuster is the second movement type for monitoring adjustment when a press on the second key is monitored, and a corresponding movement amount is acquired according to how many times the key is pressed or how long the key is pressed. Refer to FIG. 7 which is a schematic diagram illustrating the implementation of the adjuster as two keys, the adjuster includes a first upper key and a second lower key which can be pressed.

In a case where the adjuster is a knob, it can be set that the volume of ambient sounds is not increased or decreased (that is to say, is not adjusted) when a certain position on the knob is located at the upper end of the vertical central line of the housing of the phone receiver of the earphone (that is, at a rotation demarcation point), noise reduction is carried out when the knob is rotated left, and the noise reduction amount increases as the knob is rotated left and becomes maximum when the knob is rotated to the leftmost position; whereas the monitored ambient sounds are amplified when the knob is rotated right, the volume of the monitored ambient sounds increases as the knob is rotated right and becomes maximum when the knob is rotated to the rightmost position. Additionally, and in the case where the adjuster is implemented as a pushbutton or keys, noise reduction adjustment and monitoring adjustment can also be realized in a similar way.

Moreover, in addition to the above said mechanical parts (the adjuster is implemented as a rotary component (e.g. knob, rotatable disk or rotatable panel), a pushbutton or keys), a proximity-sensing touch key may also applied to carry out rotation adjustment, sliding adjustment or press adjustment.

Optionally, in accordance with another embodiment of the ambient sound adjustment method for an earphone disclosed herein, a touchpad with a multi-point touch control function may be arranged on the housing of the earphone, the touchpad is electronically connected with the main control chip of the earphone, and the noise reduction module and/or the monitoring module of the earphone are/is electronically connected with or integrated in the main control chip of the earphone.

In this case, the step of determining an adjustment type and an adjustment amount for the collected ambient sounds includes: detecting the terminal of the movement track of the finger of the user on the touchpad and determining an adjustment type and an adjustment amount for the collected ambient sounds according to the direction and the amount of displacement of the terminal of the movement track relative to a preset demarcation point between noise reduction adjustment and monitoring adjustment; determining the first adjustment type for noise reduction adjustment as an adjustment type for the ambient sounds collected when the terminal of the movement track is located on one side of the demarcation point, and determining the second adjustment type for monitoring adjustment as an adjustment type for the ambient sounds collected when the terminal of the movement track is located on the other side of the demarcation point, and determining the amount of displacement of the terminal of the movement track relative to the demarcation point as the adjustment amount.

For example, when the clockwise movement of a finger of the user is detected, the main control chip determines that the movement type is the first adjustment type for noise reduction adjustment and then determines a noise reduction amount according to the length or the angle of the movement track in reference to the preset demarcation point between noise reduction adjustment and monitoring adjustment. Contrarily, when the anticlockwise movement of a finger of the user is detected, the main control chip determines that the movement type is the second adjustment type for monitoring adjustment and then determines an amplification amount for the ambient sounds collected by the microphone according to the length or the angle of the movement track relative to the preset demarcation point between noise reduction adjustment and monitoring adjustment.

Although the adjuster is described above mainly by taking a headphone as an example, for both a headphone and an in-ear type earphone, the adjuster may also be arranged on a wire controller in the way mentioned in the above said description of the adjuster of a headphone.

A noise reduction adjustment in the ambient sound adjustment scheme for an earphone is described below, and the other aspects of the ambient sound adjustment scheme for an earphone can refer to other embodiments of the disclosure of the present invention.

Figure 8:
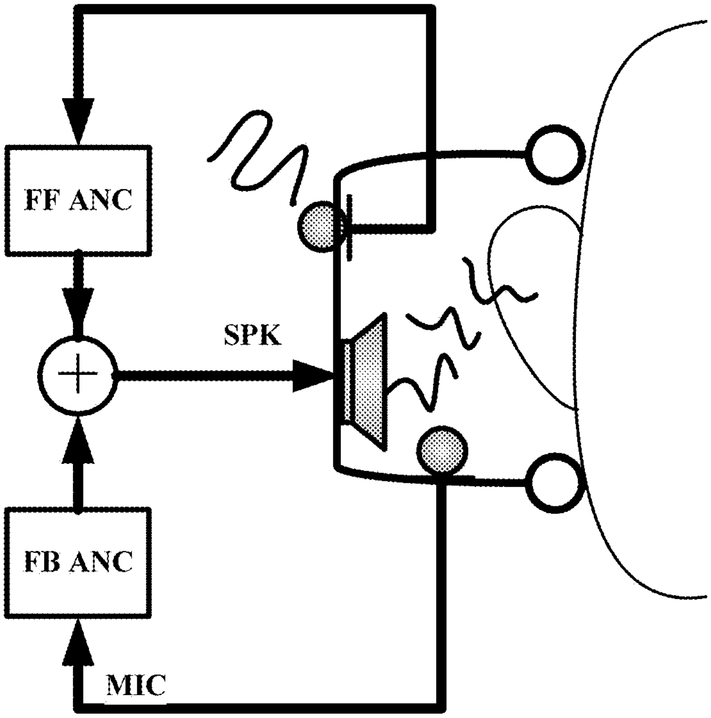
FIG. 8 is a block diagram illustrating a feedforward-feedback hybrid active noise-reducing earphone system according to another embodiment of the present invention.

FIG. 8 is a block diagram illustrating a hybrid active noise-reducing earphone system with an FF-FB noise-reducing module. The maximum noise reduction amount and the noise reduction frequency band of the hybrid active noise-reducing earphone system are overlapping of the noise reduction amount achieved by FB ANC and that achieved by FF ANC, refer to FIG. 8 which shows the basic noise reduction performance of the hybrid active noise-reducing earphone system, a noise reduction module is capable of actively reducing a quantity of noises even at a low frequency of 1000 Hz, and the maximum active noise reduction amount of the noise reduction module can reach about 25 dB, as a result, the noise-reducing earphone, when used together with an earmuff or earplug, is capable of reducing about 20 dB of noises in the whole frequency band.

The noise reduction amount/amplification amount can be changed by an adjustment circuit or software in the main control chip through changing the register in noise reduction module/monitoring module so as to achieve different grades of noise reduction/monitoring, thus, by means of the method disclosed herein, the user can manually adjust a noise reduction amount/monitoring amount.

For example, the main control chip acquires an adjustment amount for the collected ambient sounds according to the movement of the adjuster or the movement track of a finger sensed by the touchpad, for example, the main control chip, for example, which is implemented as an MCU, changes a noise reduction amount or amplification amount (that is, an adjustment amount) by modifying the value written to the register in the noise reduction module/monitoring module according to the determined adjustment amount. The noise reduction module/monitoring module amplifies and compensates for the signal picked up by a microphone (e.g. FF/FB noise-reducing MIC1 or monitoring MIC2) in the external noisy environment through a certain Equalizer (EQ) and then outputs the processed signal to the loudspeaker of the earphone used by the user. After being processed by the EQ, the low frequency of the signal is weakened while the intermediate frequency and the high frequency of the signal are enhanced so that the voice output from the earphone is more comfortable to hear.

The disclosure is described below more clearly with reference to experimental result charts.

Figure 9:
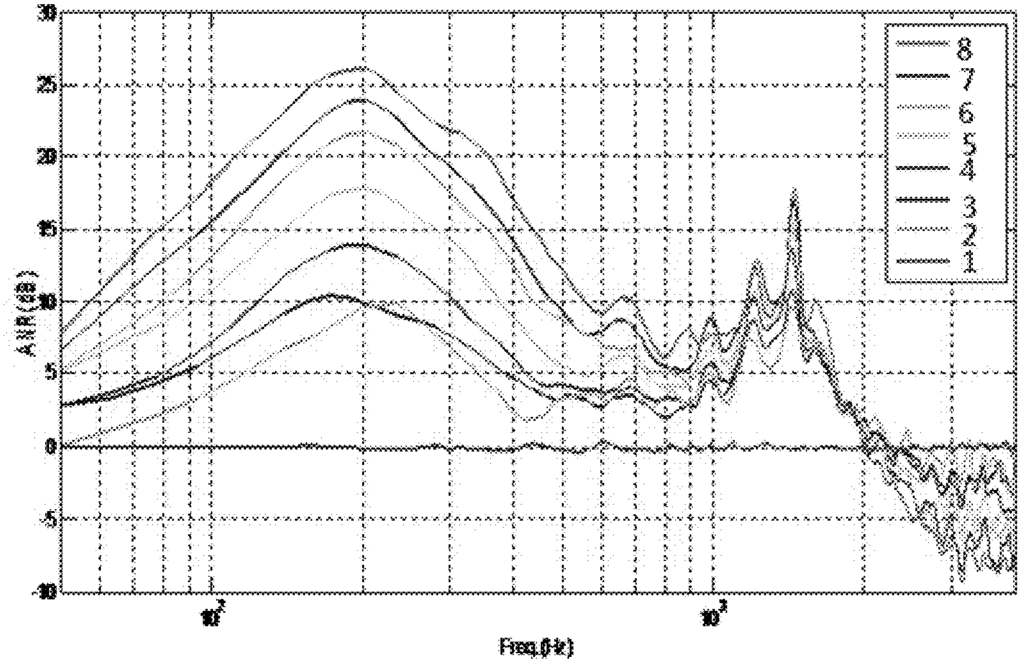
FIG. 9 is a chart showing the experiment result on the relationship between noise reduction amounts and different noise reduction grades realized by the present invention.

FIG. 9 is a chart showing the experiment result on the relationship between noise reduction amounts and different noise reduction grades achieved by the method of adjusting ambient sounds for an earphone disclosed herein. As an implementation form of the method disclosed herein, the noise reduction amount and the noise reduction frequency band needed at different grades of noise reduction can be adjusted as needed, thereby providing a better user experience. The total of the noise reduction grades can be designed according to the practical demand. In the implementation form shown in FIG. 9, the earphone disclosed herein can realize eight grades of noise reduction according to different movement amounts.

Figure 10:
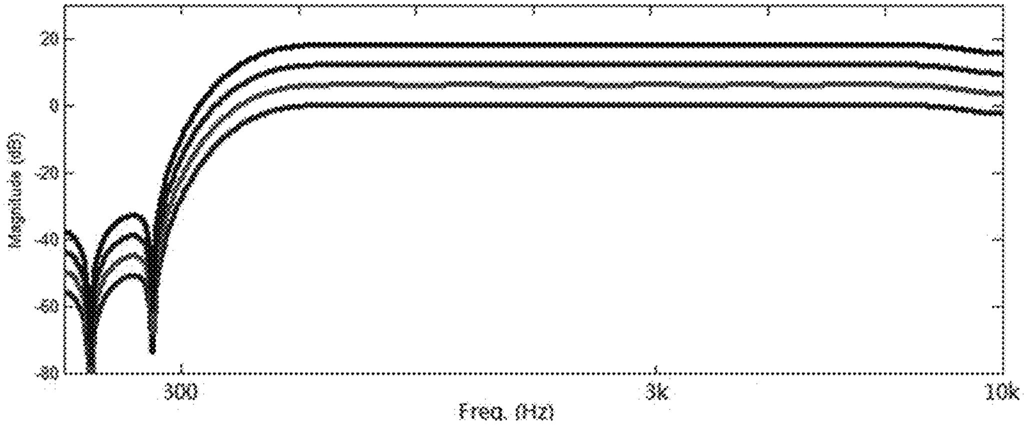
FIG. 10 is a chart showing the experiment result on the EQ curves corresponding to different monitoring grades realized by the present invention.

FIG. 10 is a chart showing the experiment result on the EQ curves corresponding to different monitoring grades realized by the method of adjusting ambient sounds disclosed herein. As an implementation form of the earphone disclosed herein, the earphone disclosed herein realizes four grades of monitoring according to different movement amounts. The total of monitoring grades, the amplification factor corresponding to a monitoring grade and the EQ curve may be designed according to different earphones or different demands of users so as to provide a better experience.

In accordance with another implementation mode of the ambient sound adjustment method for an earphone, in a case where a mechanically movable adjuster is arranged on the housing of the earphone or on the housing of the wire controller of the earphone, S201 may further include: acquiring the movement direction and the movement amount of the adjuster when the movement of the adjuster is detected, wherein the movement amount is the amount of movement of the adjuster from the former position thereof, and the movement type is determined based on the preset correspondence between movement directions and movement types. For example, in a case where the adjuster is a rotary component, the movement amount refers to the rotation angle of the adjuster relative to the former position of the adjuster; in a case where the adjuster is a pushbutton which can be pushed up and down, then the movement amount refers to the linear distance the adjuster slides from the former position thereof. Further, the correspondence between movement directions and movement types of the adjuster can be preset, for example, if the adjuster can move in two opposite directions (that is, two adjustment directions), then the movement directions of the adjuster can be referred to as a first and a second movement direction respectively, in this case, it can be preset that the movement of the adjuster along the first movement direction corresponds to a first movement type of the adjuster and the movement of the adjuster along the second movement direction corresponds to a second movement type of the adjuster. The movement type can be classified according to the function, for example, the noise reduction function or the monitoring function, of the adjuster or classified as needed, and no limitations are given to this. Here, the 'first' and the 'second', which are relative terms defined only for the sake of convenience of description, are not used to limit sequence or quantity, that is, are not to be construed as limiting the disclosure.

Correspondingly, S202 may further include: determining, based on the preset correspondence between movement types and adjustment types, the adjustment type according to the determined movement type, and calculating current adjustment amount for the collected ambient sounds according to the preset correspondence between movement amounts and adjustment amounts. For example, it can be preset that the first movement type of the adjuster corresponds to a first adjustment type for noise reduction adjustment and the second movement type of the adjuster corresponds to a second adjustment type for monitoring adjustment, in this way, the volume of the ambient sounds is reduced and the adjustment type is determined to be noise reduction adjustment when the movement of the adjuster belongs to the first movement type, and the volume of the ambient sounds is increased and the adjustment type is determined to be monitoring adjustment when the movement of the adjuster belongs to the second movement type. For example, if the ambient sound adjustment range of the adjuster is from −30 dB to +20 dB, in a case where the adjuster is implemented as a rotary component, it can be preset that the rotation of the adjuster along the anticlockwise direction (that is, the first movement direction) (corresponding to the first movement type) corresponds to the first adjustment type for noise reduction adjustment, and the rotation of the adjuster along the clockwise direction (that is, the second movement direction) (corresponding to the second movement type) corresponds to the second adjustment type for monitoring adjustment, thus, the volume of the ambient sounds is gradually decreased as the adjuster rotates along the anticlockwise direction and thus the ambient sounds of are suppressed from +20 dB to −30 dB, and the volume of the ambient sound is gradually increased as the adjuster rotates along the clockwise direction and thus the ambient sounds are magnified from −30 dB to +20 dB. Besides, as the ambient sound adjustment range adjusted by the adjuster of an earphone is generally fixed after the earphone is manufactured, the correspondence between the movement range and the ambient sound adjustment range of the adjuster is usually fixed, and generally, the movement range of the adjuster is in proportion to the ambient sound adjustment range of the adjuster, for example, if the ambient sound adjustment range of the adjuster is between −30 dB and +20 dB, the ambient sound adjustment amount of the adjuster gradually changes from +20 dB to −30 dB as the adjuster rotates anticlockwise gradually from 0 degree to 360 degrees from a certain position and from −30 dB to +20 dB as the adjuster gradually rotates clockwise from 0 degree to 360 degrees from the certain position, that is, the bigger the movement amount of the adjuster is, the bigger the ambient sound adjustment amount of the adjuster is, and vice versa. Thus, after the movement amount of the adjuster is acquired, an adjustment amount for the ambient sounds can be acquired by making a simple calculation.

In the above embodiments, the adjuster may be implemented as the above mechanically movable rotary component (e.g. knob, rotatable disk and rotatable panel component), pushbutton, keys or a proximity-sensing touch key. In the foregoing embodiment, the adjustment of the adjuster is realized more easily because any adjustment made to reduce the ambient sounds relative to the situation before the adjustment is made is a noise reduction adjustment, and any adjustment made to amplify the ambient sounds relative to the situation before the adjustment is made is a monitoring adjustment, in no need of setting a demarcation point (e.g. a rotation demarcation point or a route demarcation point used in the above embodiments), in this way, in the actual effect charts shown in FIG. 9 and FIG. 10, there are 12 noise reduction grades, that is, the sum of the eight grades shown in FIG. 9 and the four grades shown in FIGS. 10, and 12 monitoring grades, that is, the sum of the eight grades shown in FIG. 9 and the four grades shown in FIG. 10.

Optionally, in a case where the adjuster is a touchpad with a multi-point touch control function which is arranged on the housing of the earphone, the step of determining an adjustment type and an adjustment amount for the collected ambient sounds may include: detecting the movement track and the movement direction of a finger of the user on the touchpad; determining the adjustment amount for the collected ambient sounds according to the detected movement track; and determining, based on the preset correspondence between movement directions and adjustment types, the adjustment type according to the detected movement direction, wherein the adjustment type for the collected ambient sounds includes a first adjustment type corresponding to noise reduction adjustment and a second adjustment type corresponding to monitoring adjustment. For example, if the clockwise movement of a finger of the user is detected, the first adjustment type for noise reduction adjustment is determined as the adjustment type for the collected ambient sounds, and a noise reduction amount is determined according to the length or the angle of the movement track. Contrarily, if the anticlockwise movement of a finger of the user is detected, the second adjustment type for monitoring adjustment is determined as the adjustment type for the collected ambient sounds, and then an amplification amount is determined for the ambient sounds collected by the microphone according to the length or the angle of the movement track.

In accordance with another implementation form of the ambient sound adjustment method for an earphone provided herein, in a case where an earphone application client is installed on a terminal, the step of determining an adjustment type and an adjustment amount for the collected ambient sounds may include: receiving, from the earphone application client on the terminal, an adjustment type and an adjustment amount for the collected ambient sounds; and controlling, according to the adjustment type, a noise reduction module or a monitoring module to adjust the collected ambient sounds by the adjustment amount. The adjustment type for the collected ambient sounds includes a first adjustment type corresponding to noise reduction adjustment and a second adjustment type corresponding to monitoring adjustment. Optionally, the ambient sound adjustment method for an earphone of the present invention may further include: receiving a playing volume from the earphone application client installed on the terminal, and setting the power amplifier of the earphone according to the playing volume.

In the foregoing embodiment, the terminal may be a computer, a laptop, a mobile phone or a PAD. In the embodiment, an adjustment type and an adjustment amount for the collected ambient sounds are set in the earphone application client and transmitted to the main control chip of the earphone so that the main control chip acquires the adjustment type and the adjustment amount and then controls the noise reduction module or the monitoring module to carry out noise reduction adjustment or monitoring adjustment. Here, information can be transmitted between the earphone and the terminal in existing communication ways, for example, through a Bluetooth device, a network protocol or WIFI.

By detecting the movement of the adjuster to obtain a plurality of gradually varied movement amounts (the difference between two successive movement amounts may be equal or not), and different movement amounts are corresponding to different adjustment amounts, so the ambient sound adjustment method for an earphone of the present invention enables the user to adjust a noise reduction amount or the monitoring volume of the collected ambient sounds as needed, thus solving the problems brought about by existing earphones whose noise reduction function can only be simply activated or deactivated, realizing the flexible ambient sound adjustment of earphones, making earphones more functionally human-oriented and improving the performance of earphones as well as user experience.

Further, in some cases, the user desires for a rapid direct switching from a noise reduction mode to an ambient sound monitoring mode and then for a rapid recovery of the noise reduction mode after monitoring the ambient sounds for a period of time, for example, it may take the wearer of the earphone who is listening to music in the noise reduction mode a little time to switch, in a rotation adjustment manner, the mode of the earphone from the noise reduction mode to the monitoring mode to have a short communication with someone, and it also takes the wearer a little time to change the noise reduction grade of the earphone back to the former noise reduction grade after the communication is done, for this sake, the ambient sound adjustment method for an earphone of the present invention also provides a technical solution to the rapid switching to a monitoring mode.

Figure 11:
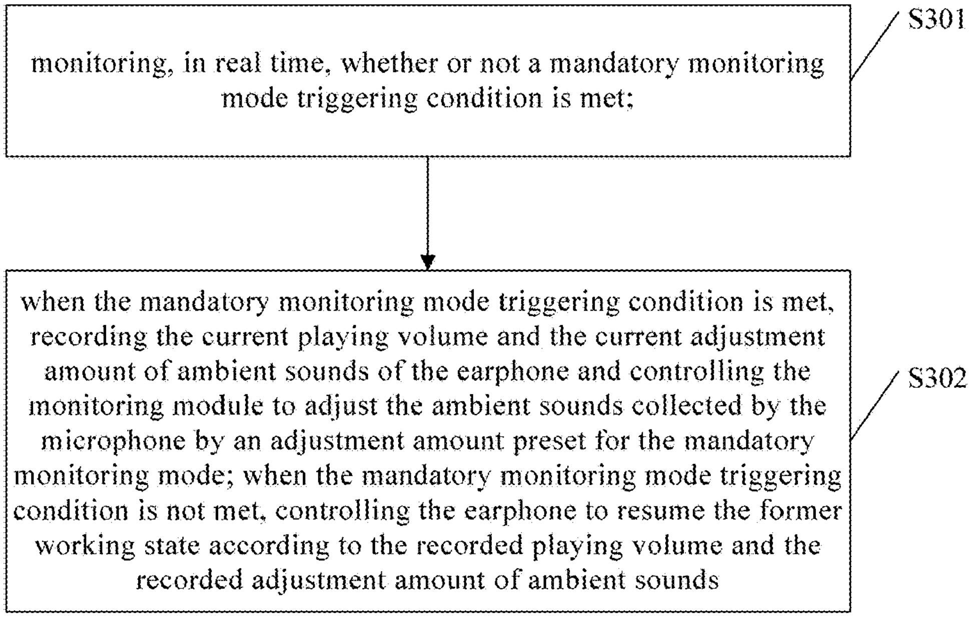
FIG. 11 is a schematic diagram illustrating a method for triggering a mandatory monitoring mode according to another embodiment of the present invention.

FIG. 11 shows an implementation mode of a mandatory monitoring mode trigger method, and the ambient sound adjustment method for an earphone disclosed herein may include the following steps:

S301: monitoring, in real time, whether or not a mandatory monitoring mode triggering condition is met;

S302: recording the current playing volume and the current adjustment amount of ambient sounds of the earphone and adjusting the collected ambient sounds by an adjustment amount preset for the mandatory monitoring mode when the mandatory monitoring mode triggering condition is met, whereas controlling the earphone to resume the former working state according to the recorded playing volume and the recorded adjustment amount of ambient sounds when the mandatory monitoring mode triggering condition is not met. Here, the ambient sound adjustment amount preset for a mandatory monitoring mode is a fixed value, generally a very large decibel value, for example, a value above the maximum monitoring grade, so that the user of the earphone can hear ambient sounds clearly even when wearing the earphone.

Optionally, the ambient sound adjustment method for an earphone disclosed herein may further include: adjusting the playing volume of the earphone to a playing volume preset for the mandatory monitoring mode when the mandatory monitoring mode triggering condition is met. This adjustment is suitable for a user who is listening to music in a noise reduction mode or in a purely playing mode and hopes to continue to listen to music after the mandatory monitoring mode is triggered, in this situation, apart from that the monitoring module is controlled to adjust the ambient sounds according to the amplification amount preset for the mandatory monitoring mode, the music is still played at the playing volume preset for the mandatory monitoring mode, here, the preset playing volume is a fixed value, generally, a relatively low value, so that the user can hear ambient sounds clearly. The adjuster may be implemented as any one kind of the following components: a capacitive touch-sensing switch, a resistive touch-sensing switch, a proximity-sensing switch, a pressure sensing switch, a mechanical switch, a rotatable panel switch and a metal sheet type touch switch. The proximity-sensing switch is, for example, an infrared proximity-sensing switch. The mechanical switch is, for example, a button-type mechanical switch, a knob-type mechanical switch or a pushbutton-type mechanical switch.

In a case where the adjuster is implemented as, for example, a plurality of metal sheet type touch switches, a plurality of capacitive touch-sensing switches, a plurality of resistive touch-sensing switches or a plurality of proximity-sensing switches, S301 of monitoring, in real time, whether or not a mandatory monitoring mode triggering condition is met may be a step of monitoring, in real time, whether or not the housing of the earphone is covered by a palm of the user. For example, it can be set that the mandatory monitoring mode of the earphone is triggered to cause the earphone to enter the mandatory monitoring mode when the covering of the housing of the phone receiver of the earphone by a palm is sensed by the adjuster and that the earphone exits the mandatory monitoring mode to resume the former working state automatically and quickly when the adjuster senses the departure of the palm from the housing of the phone receiver of the earphone; optionally, the switching between the mandatory monitoring mode and non-mandatory monitoring mode (i.e., the mode except the mandatory monitoring mode) is conducted based on the change sensed by the adjuster, for example, in the case that the earphone is not in the mandatory monitoring mode at present, the adjuster sensed a palm has covered the housing of the phone receiver of the earphone for a certain time (e.g. 2 seconds) from the housing of the earphone and then departed from the housing of the earphone, then a quick switching from the current working state to the mandatory monitoring mode is triggered; in the case that the earphone is in the mandatory monitoring mode at present, the adjuster sensed a palm has covered the housing of the phone receiver of the earphone for a certain time (e.g. 2 seconds) from the housing of the earphone and then departed from the housing of the earphone, then a quick switching from the mandatory monitoring mode to the former working state is triggered. It should be noted that the covering of the housing of the phone receiver of the earphone by a palm may be covering the most part of the surface of the housing of the phone receiver of the earphone by a palm or covering the whole housing of the phone receiver of the earphone by a palm, and no specific limitations are given to this.

Moreover, optionally, in a case where the adjuster is implemented as, for example, a plurality of metal sheet type touch switches, a plurality of capacitive touch-sensing switches or a plurality of resistive touch-sensing switches or a plurality of proximity-sensing switches, a plurality of pressure sensing switches, mechanical switch or rotatable panel type switch, a mandatory monitoring mode triggering button, for example, a mechanical button for activating the mandatory monitoring mode, may be arranged on the housing of the earphone so that the user can press the mechanical button to cause the earphone to enter the mandatory monitoring mode and press the mechanical button again to cause the earphone to exit the mandatory monitoring mode. Not limited to achieve the foregoing purpose, the mechanical button may also realize the switching among a playing mode, a noise reduction and monitoring adjustment mode, and a mandatory monitoring mode, for example, the button is pressed once for switching into the play mode, twice for switching into the noise reduction and monitoring adjustment mode, and three times for switching into the mandatory monitoring mode, it can also be set that the earphone switches into the mandatory monitoring mode after the mechanical button is pressed for a certain time. Although certain embodiments of the triggering of the mandatory monitoring mode are described above, no limitations are given to the triggering of the mandatory monitoring mode, and any method capable of realizing the switching between the mandatory monitoring mode and other mode should fall within the scope of the disclosure.

Optionally, in a case where the adjustment type and the adjustment amount are received from the earphone application client installed on a terminal, the step S301 of monitoring, in real time, whether or not a mandatory monitoring mode triggering condition is met may be a step of monitoring, in real time, whether a command of entering the mandatory monitoring mode or a command of exiting the mandatory monitoring mode is received from the earphone application client installed on the terminal. When the earphone receives a command of entering the mandatory monitoring mode from the earphone application client installed on the terminal, the current playing volume and the current ambient sound adjustment amount of the earphone are recorded, and the ambient sounds collected by the microphone is adjusted by an ambient sound adjustment amount preset for a mandatory monitoring mode; when the earphone receives a command of exiting the mandatory monitoring mode from the earphone application client installed on the terminal, the earphone is controlled according to the recorded playing volume and the recorded ambient sound adjustment amount to resume the former working state thereof. The ambient sound adjustment amount preset for the mandatory monitoring mode may be included in and sent with the command of entering the mandatory monitoring mode, however, the disclosure is not limited to this. Optionally, the earphone may receive a playing volume preset for the mandatory monitoring mode when receiving the command of entering the mandatory monitoring mode from the earphone application client installed on the terminal, and then adjust the playing volume thereof to the playing volume preset for the mandatory monitoring mode. The playing volume preset for the mandatory monitoring mode may be, for example, included in the command of entering the mandatory monitoring mode, however, the disclosure is not limited to this.

In the above embodiments, an earphone provided with a noise reduction mode and a monitoring mode may have the following five working modes: a pure audio playing mode, a pure noise reduction mode, a noise-reducing and audio-playing mode, a pure monitoring mode and a monitoring and audio-playing mode. The pure noise reduction mode is suitable for the user to use in a noisy environment. In this mode, the earphone just denoises the ambient sounds, playing no audios such as music, that is, the playing volume of the earphone is 0. The pure audio playing mode refers to a mode in which the earphone only plays audios such as music, adjusting no ambient sounds (for example, corresponding to the above-mentioned location of the knob at a vertical central line), that is, in this mode, the ambient sound adjustment amount of the earphone is 0 dB; the pure monitoring mode is a mode in which the earphone only monitors ambient sounds, playing no audios such as music, that is, the playing volume of the earphone in this mode is 0; the noise-reducing and audio-playing mode is a mode in which ambient sounds are denoised while a playing volume is provided; and the monitoring and audio-playing mode is a mode in which ambient sounds are monitored while a playing volume is provided. The noise reduction mode mentioned herein may include the noise-reducing and audio-playing mode and the pure noise reduction mode, and the monitoring mode mentioned herein may include the pure monitoring mode and the monitoring and audio-playing mode.

In accordance with another aspect of the disclosure in the present invention, an earphone is provided. The earphone includes at least one microphone, an adjusting device, a main control chip, and a noise reduction module and/or a monitoring module.

The microphone is arranged on the external side of the earphone to collect ambient sounds. The adjusting device is adapted to adjust the ambient sounds collected by the microphone, and it is generally manually adjusted by the user so as to adjust the ambient sounds collected by the microphone. For example, as stated above, the adjusting device may be implemented as a mechanically movable adjuster, for example, as a rotatable component (e.g. knob), a pushbutton or a key (or keys). In addition, the adjusting device may also be implemented as a touchpad with a multi-point touch control function, or as an earphone application client installed on a terminal.

The main control chip is adapted to monitor the adjustment of the adjusting device and determine an adjustment type and an adjustment amount for the collected ambient sounds according to the adjustment of the adjusting device. For example, the main control chip may be implemented as an MCU or a DSP.

The noise reduction module and/or the monitoring module are/is adapted to carry out noise reduction adjustment and/or monitoring adjustment for the collected ambient sounds by the determined adjustment amount according to the adjustment type determined by the main control chip. For example, the noise reduction module and/or the monitoring module may be implemented as ANC chips or an ANC chip.

The noise reduction module and the monitoring module may be components independent from but electronically connected with the main control chip or integrated in the main control chip.

According to an embodiment of the earphone of the present invention, the adjusting device may be a mechanically movable adjuster arranged on the housing of the earphone, wherein the adjuster is equipped with an electrical port through which the adjuster is electronically connected with the noise reduction module and/or the monitoring module of the earphone. The main control chip monitors the movement behavior of the adjuster in real time, acquires the movement amount and the movement type of the adjuster when the adjuster moves, determines a current adjustment type according to the acquired movement type and determines a current adjustment amount for ambient sounds according to the acquired movement amount. Then, the main control chip sends the determined adjustment type and adjustment amount to the noise reduction module or the monitoring module to control the noise reduction module or the monitoring module to adjust the collected ambient sounds by the determined adjustment amount.

In the foregoing embodiment, in a case where the adjuster is implemented as a rotatable component (e.g. knob), a rotation demarcation point is set on the rotation track of the rotatable component, the main control chip determines that the movement type of the rotatable component is the first movement type when detecting the rotation of the rotatable component towards a preset side of the rotation demarcation point or that the movement type of the rotatable component is the second movement type when detecting the rotation of the rotatable component towards the other side of the rotation demarcation point, and acquires a movement amount based on the rotation amount of the rotatable component relative to the rotation demarcation point.

In the foregoing embodiment, in a case where the adjuster is implemented as a pushbutton, a route demarcation point is set on a push route of the adjuster, the main control chip determines that the movement type of the pushbutton is the first movement type when detecting the sliding of the pushbutton towards a preset side of the route demarcation point or that the movement type of the pushbutton is the second movement type when detecting the sliding of the pushbutton towards the other side of the route demarcation point, and acquires a movement amount based on the distance the pushbutton slides from the route demarcation point.

In the foregoing embodiment, the adjuster may also be implemented as a first and a second key, in this case, the main control chip determines the movement type of the adjuster to be the first movement type when detecting the pressing on the first key or that the movement type of the adjuster is the second movement type when detecting the pressing on the second key, and a corresponding movement amount is acquired, for example, according to the times the first/second key is pressed. For example, the correspondence between the times the key is pressed and movement amounts may be set in advance.

Optionally, the adjuster is arranged on the housing of the phone receiver of a headphone, and when implemented as a knob, the adjuster may be assembled with the phone receiver coaxially or not.

In accordance with another embodiment of the earphone of the present invention, the adjusting device may be a touchpad with a multi-point touch control function which is arranged on the housing of the earphone, the touchpad is electronically connected with the main control chip of the earphone, and the noise reduction module and/or the monitoring module of the earphone are/is electronically connected with or integrated in the main control chip of the earphone. The touchpad detects the terminal of the movement track of a finger of the user. The main control chip determines the current adjustment type and the current adjustment amount for the ambient sounds according to the direction and the amount of displacement of the terminal of the movement track relative to a preset demarcation point between the noise reduction adjustment area and the monitoring adjustment area. When the terminal of the movement track is located on one side of the demarcation point, the adjustment type for the collected ambient sounds is the first adjustment type corresponding to noise reduction adjustment, and when the terminal of the movement track is located on the other side of the demarcation point, the adjustment type for the collected ambient sounds is the second adjustment type corresponding to monitoring adjustment, and the amount of the displacement of the terminal of the movement track from the demarcation point is the adjustment amount.

In accordance with another embodiment of the earphone of the present invention, in a case where the adjusting device is a mechanically movable adjuster arranged on the housing of the earphone or on the housing of the wire controller of the earphone, the main control chip acquires the movement direction and the movement amount of the adjuster when the movement of the adjuster is monitored, wherein the movement amount is the amount of movement of the adjuster from the former position thereof, and the movement type is determined based on the preset correspondence between movement directions and movement types; and the main control chip determines, based on the preset correspondence between movement types and adjustment types, the adjustment type according to the determined movement type and calculates the current adjustment amount for the collected ambient sounds according to the preset correspondence between movement amounts and adjustment amounts.

In a case where the adjuster is a touchpad with a multi-point touch control function which is arranged on the housing of the earphone, the touchpad is electronically connected with the main control chip of the earphone to detect the movement track and the movement direction of a finger of the user on the touchpad; the main control chip also determines an adjustment amount for the collected ambient sounds according to the detected movement track and determines, based on the preset correspondence between movement directions and adjustment types, an adjustment type according to the detected movement direction; wherein the adjustment type for the collected ambient sounds includes a first adjustment type corresponding to noise reduction adjustment and a second adjustment type corresponding to monitoring adjustment. For example, if the clockwise movement of a finger of the user is detected, the main control chip determines that the adjustment type is the first adjustment type for noise reduction adjustment and determines a noise reduction amount according to the length or the angle of the movement track. Contrarily, if the anticlockwise movement of a finger of the user is detected, the main control chip determines that the adjustment type is the second adjustment type for monitoring adjustment and determines an amplification amount for the ambient sounds collected by the microphone according to the length or the angle of the movement track.

In the foregoing embodiment, the touchpad with a multi-point touch control function may be implemented as, but are not limited to be implemented as one kind of the following components: a plurality of metal sheet type touch switches, a plurality of capacitive touch-sensing switches, a plurality of resistive touch-sensing switches or a plurality of proximity-sensing switches, and any other similar components.

Optionally, the present invention provides an earphone, including: a mandatory monitoring mode triggering module arranged on the housing of the earphone to receive the triggering of a mandatory monitoring mode by the user; a main control chip configured to monitor, in real time, the output from the mandatory monitoring mode triggering module, determine whether or not a mandatory monitoring mode triggering condition is met according to the output from the mandatory monitoring mode triggering, and if so, record the current playing volume and the current adjustment amount of the ambient sounds and control the monitoring module to adjust the ambient sounds collected by a microphone by an preset adjustment amount of the ambient sounds in the mandatory monitoring mode, otherwise, control the earphone to resume the former working state thereof according to the recorded playing volume and the recorded adjustment amount of ambient sounds. Optionally, the main control chip may also be adapted to adjust the playing volume of the earphone to the preset one when monitoring that the mandatory monitoring mode triggering condition is met.

The mandatory monitoring mode triggering condition is related to the type of the adjuster, for example, as stated above, in a case where the adjuster is implemented as a touchpad with a multi-point touch control function, the mandatory monitoring mode may be triggered through the covering of the housing of the earphone by a palm of the user, for example, the mandatory monitoring mode is triggered when the touchpad detects the covering of the touchpad by a palm of the user, then the main control chip controls the earphone to enter the mandatory monitoring mode, and on the contrary, the main control chip controls the earphone to exit the mandatory monitoring mode when the touchpad detects the palm of the user goes away from the touchpad, and goes back to the former working state with the recorded playing volume and the recorded adjustment amount of the ambient sounds. The other detail can refer to the above related description of the ambient sound adjustment method for an earphone and is therefore not described repeatedly here for the simplicity.

An implementation form of a mandatory monitoring mode according to an embodiment of the present invention is described below with reference to FIG. 12, for example, the adjuster is implemented as a plurality of metal sheet type touch switches, for example, a plurality of metal sheet type touch-detecting capacitors that are arranged on the housing of a phone receiver of a headphone, in this case, the adjuster may not only adjust ambient sounds, but also may serve as a mandatory monitoring triggering module for triggering a mandatory monitoring mode when detecting that a palm of the user covers or goes away from the housing of the earphone. In the embodiment shown in FIG. 12, the capacitance of every or most of metal sheet type touch-detecting capacitors is brought about to be changed by covering of a palm of the user with or going away of a palm of the user from the housing of the earphone, the main control chip monitors, in real time, the capacitance output from the metal sheet type touch-detecting capacitors, determines whether or not the capacitance output from the metal sheet type touch-detecting capacitors is equal to or greater than a preset threshold and, if so, determines that the mandatory monitoring mode triggering condition is met, otherwise, determines that the mandatory monitoring mode triggering condition is not met.

In this way, with the use of a touchpad with a multi-point touch control function, the noise reduction amount of the earphone or the volume of the monitored ambient sounds can be adjusted gradually, moreover, a mandatory monitoring mode can be triggered quickly and the former noise-reducing and audio-playing mode can be recovered fast, thus providing a more functionally human-oriented, good user experience, and improving the earphone control function.

Optionally, in a case where the adjuster is implemented as one kind of the following components, for example, a plurality of metal sheet type touch switches, a plurality of capacitive touch-sensing switches, a plurality of resistive touch-sensing switches or a plurality of a proximity-sensing switches, a plurality of pressure sensing switches, mechanical switch, or rotatable panel switch, a mechanical button is arranged on the housing of the earphone to trigger if the earphone enters the a mandatory monitoring mode or not.

Figure 13:
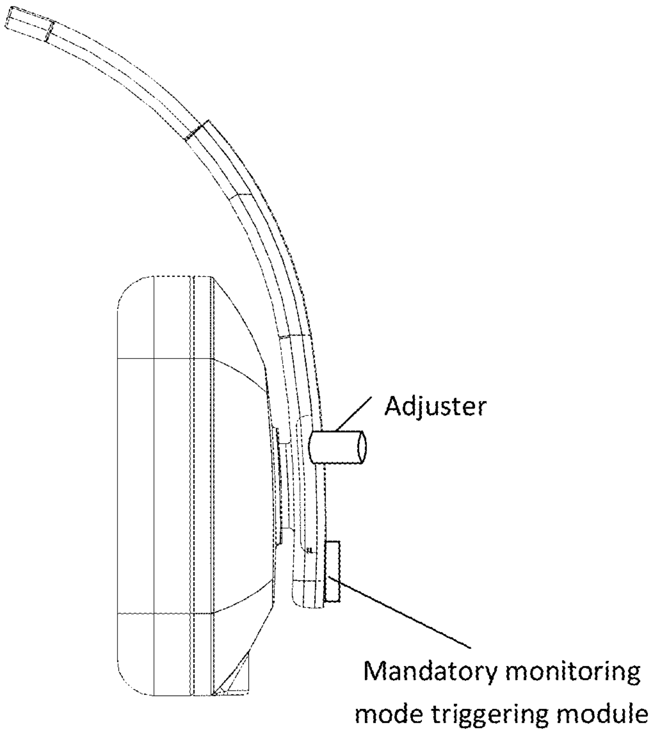
FIG. 13 is a schematic diagram illustrating another implementation form of a mandatory monitoring mode triggering module according to another embodiment of the present invention.

FIG. 13 is a schematic diagram illustrating an implementation form of a mandatory monitoring mode triggering module according to one embodiment of the present invention. The mandatory monitoring mode triggering module is a mechanical knob type switch which is arranged on the housing of the phone receiver of an earphone and protrudes from the external side of the housing of the phone receiver by a certain height so as to be held conveniently. When the mechanical knob type switch rotates till different areas, it will trigger different modes, the different modes may include a playing volume adjustment mode, an ambient sound adjustment mode and a mandatory monitoring mode, or may include the mandatory monitoring mode and the playing volume adjustment mode, or may include the mandatory monitoring mode and the ambient sound adjustment module. Optionally, the mandatory monitoring mode triggering module may also be implemented as a mechanical pushbutton type switch. These implementation forms can refers to the above related description of the ambient sound adjustment method, and are therefore not described again for the simplicity.

Figure 12:
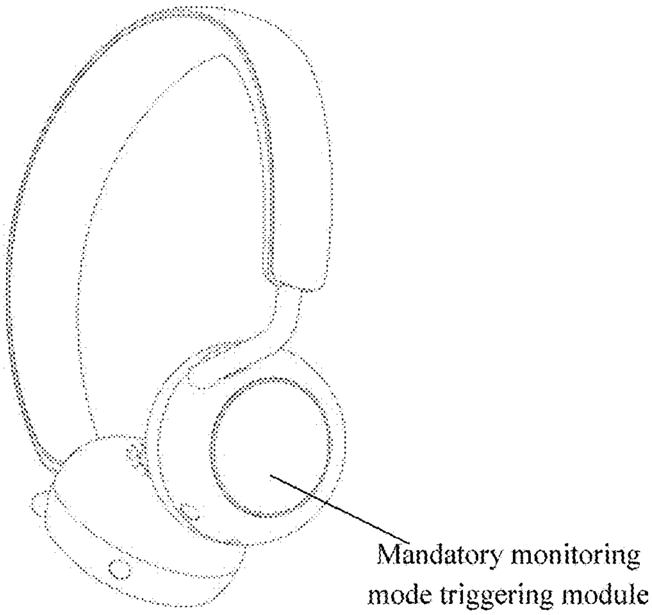
FIG. 12 is a schematic diagram illustrating one implementation form of a monitoring mode triggering module according to one embodiment of the present invention.

FIG. 12 and FIG. 13 illustrate a mandatory monitoring mode triggering module mainly by taking a headphone as an example, but for an in-ear type earphone or a headphone, a mandatory monitoring mode triggering module may be arranged on the housing of the wire controller of the headphone.

Equipped with a mandatory monitoring mode triggering module, a headphone of the present invention can enter a mandatory monitoring mode immediately from a noise reduction mode and quickly resume the former working state when a mandatory monitoring triggering condition is not met, thus, the headphone of the present invention not only meets the demand of the user on the gradual control and adjustment of ambient sounds but also realizes the fast switching between the mandatory monitoring mode and the former working mode and consequentially provides a more functionally human-oriented user experience and improves the earphone control function.

The present invention also provides another embodiment of the earphone in which the above adjusting device and the above mandatory monitoring mode triggering module may both be realized by an earphone application client installed on a terminal.

In accordance with an embodiment of the present invention, an earphone is provided which includes at least one microphone, a receiving device, a main control chip and a noise reduction module and/or a monitoring module.

The at least one microphone is arranged on the external side of the earphone to collect ambient sounds.

The receiving device is arranged to receive an adjustment type and an adjustment amount sent from an earphone application client installed on a terminal for adjusting the collected ambient sounds. The adjustment type for the collected ambient sounds includes, but is not limited to: a first adjustment type corresponding to noise reduction adjustment and a second adjustment type corresponding to monitoring adjustment. The receiving device may be, for example, a Bluetooth device, a gateway device, a WIFI device or an infrared device, but no limitation is given to the receiving device.

The main control chip is adapted to determine the adjustment type and the adjustment amount received by the receiving device.

The noise reduction module and/or the monitoring module are/is adapted to carry out noise reduction adjustment and/or monitoring adjustment for the collected ambient sounds using the determined adjustment amount according to the determined adjustment type.

In accordance with the foregoing embodiment of earphone in the present invention, a mandatory monitoring mode may be triggered through the arrangement of the foregoing mandatory monitoring mode triggering module or through the receiving of a mandatory monitoring mode command from the earphone application client installed on a terminal, and no limitations are given to this.

The disclosure also provides a terminal which includes: an earphone application client and a transmitting device, wherein the earphone application client is installed on the terminal to provide, on the interface thereof, a first virtual adjuster which can be touched to set an adjustment type and an adjustment amount for ambient sounds and a second virtual adjuster which can be touched to set a playing volume, wherein the adjustment type for ambient sounds includes a first adjustment type corresponding to noise reduction adjustment and a second adjustment type corresponding to monitoring adjustment; and the transmitting device is configured to send a set adjustment type and a set adjustment amount for ambient sounds and a set playing volume to the earphone. The transmitting device may be, for example, a Bluetooth device, a gateway device, a WIFI device, or an infrared device, and no limitations are given to this. Optionally, the first virtual adjuster and/or the second virtual adjuster may be implemented as any one of: virtual knobs (knob), virtual pushbuttons (pushbutton) or two virtual keys.

Further, in a case where the first virtual adjuster and the second virtual adjuster are implemented as two virtual keys, a command of entering a mandatory monitoring mode is sent to the earphone once the earphone detects that the two virtual keys are pressed at the same time, and a command of exiting a mandatory monitoring mode is sent to the earphone once the earphone detects that the two virtual keys are released at the same time.

Optionally, the first virtual adjuster and the second virtual adjuster may be implemented as one virtual adjuster, in this case, a virtual selecting switch is arranged on the virtual adjuster to realize the switching among a playing volume adjustment mode, an ambient sound adjustment mode and a mandatory monitoring mode.

Optionally, the mandatory monitoring triggering module mentioned herein may be used together with and cooperate with an earphone application client installed on a terminal, and the related settings about the mandatory monitoring triggering module and the earphone application client can be made by those of ordinary skill in the art on the basis of the disclosure and are therefore not described here repeatedly.

In the above description of embodiments of the earphone and the terminal, some details can refer to the related description of the ambient sound adjustment method for an earphone and are therefore not described here repeatedly for the simplicity.

In conclusion, the disclosure at least has the following advantages:

1: as the adjuster is implemented as a mechanical member, the user can manually adjust noise reduction grade and monitoring grade, besides, the adjuster is implemented as one mechanical member so as to make its structure simple but have more functions;

2: as the adjuster can be mechanically implemented as a knob, a pushbutton, two independent keys, or any other components capable of realizing the same functions, the adjuster can be implemented flexibly;

3: the user can adjust the amount of noise reduction and the volume of the ambient sounds monitored using a knob, a pushbutton, or the mixture of an upper key and a lower key, thus solving the problem that existing earphones only provide a noise reduction function activation and a noise reduction function deactivation in terms of noise reduction and a monitoring function activation and a monitoring function deactivation in terms of monitoring and consequentially providing a more functionally human-oriented and better user experience.

4: the present invention may provide a function of fast entering the mandatory monitoring mode and a function of fast recovering the former noise-reduction and audio-playing mode to meet the temporary or sudden monitoring requirement of the user, thus providing a better user experience and a better earphone control function.

5: The present invention may use a mechanically adjustable adjuster, or a terminal-provided virtual adjuster, or both of a mechanically adjustable adjuster and a terminal-provided virtual adjuster to realize the purposes of the present invention.

It should be understood that the above units or modules can be implemented in various forms, for example, the noise reduction module, the monitoring module, and a mandatory monitoring mode triggering module can be realized by an instruction configuration processor. The above modules may be independent from or integrated with each other.

The present invention can be a system, a method, or include computer program products. Computer program products may include computer-readable storage medium on which computer-readable program instructions are recorded for processor to realize each aspect of the present invention. The computer-readable program instructions for executing the operations involved herein may be assembly instructions, Instruction Set Architecture (ISA) instructions, machine instructions, machine-related instructions, microcodes, firmware instructions, status setting data, or source/target codes written using one programming language or the combination of several programming languages, and the programming languages include object-oriented programming languages such as Smalltalk, C++, and common procedural programming languages such as the C language or the like. The computer-readable program instructions may be totally or partially executed on the computer of a user, or executed as an independent software package, or executed partially on the computer of a user and partially on a remote computer or totally executed on a remote computer or server.

Each aspect of the present invention is described herein with reference to the flowcharts and/or block diagrams of the method, device (system) and computer program products disclosed herein. It should be noted that the blocks in the flowcharts and/or block diagrams and the combinations of the blocks can be realized by computer-readable program instructions.

The flowcharts and the block diagrams included in the accompanying drawings show the architecture, the functions and the operations that may be achieved by the systems, methods and computer program products according to the embodiments of the present invention. In this regard, each block in the flowcharts or block diagrams represents a part of a module, a program segment or an instruction which includes one or more executable instructions for realizing a specific logic function. In some substitutive implementations, the functions marked in the blocks may be realized in a sequence different from that marked in the accompanying drawings. For example, two successive blocks may be actually executed substantially in parallel or in a reverse sequence, depending on the functions practically needed. It should also be noted that the blocks in the flowcharts and/or block diagrams and the combinations thereof may be realized by a specific hardware-based system for executing a specific function or action or by the combination of specific hardware and computer instructions. It is well known to those of ordinary skill in the art that the realization of these blocks by hardware, software or the combination of software and hardware is equivalent.

While certain embodiments have been described, it should be understood by those of ordinary skill in the art that these embodiments have been presented by way of example only, and are not intended to limit the scope of the disclosure, and that modifications can be made to the embodiments described herein without departing from the spirit of the present invention. The scope of the present invention is limited by accompanying claims.

What is claimed is:

1. A method of adjusting ambient sounds for an earphone, wherein the earphone collects ambient sounds using at least one external microphone, and the method comprises:

determining an adjustment type and an adjustment amount for the collected ambient sounds; and adjusting, according to the determined adjustment type, the collected ambient sounds by the determined adjustment amount;

wherein a mechanically movable adjuster is arranged on a housing of the earphone or on a housing of a wire controller of the earphone, the adjuster is equipped with an electrical port through which the adjuster is electronically connected with a noise reduction module and/or a monitoring module of the earphone;

the step of determining the adjustment type and the adjustment amount for the collected ambient sounds comprises:

monitoring a movement behavior of the adjuster in real time and acquiring a movement amount and a movement type of the adjuster if the adjuster moves;

determining a current adjustment type for the collected ambient sounds according to the acquired movement type and determining a current adjustment amount for the collected ambient sounds according to the acquired movement amount.

2. The method according to claim 1, wherein, the step of acquiring the movement amount and the movement type of the adjuster if the adjuster moves comprises:

acquiring a movement direction and the movement amount of the adjuster when the movement of the adjuster is monitored, wherein the movement amount is the amount of movement of the adjuster from the former position thereof, and the movement type is determined based on a preset correspondence between movement directions and movement types; and the step of determining the current adjustment type for the collected ambient sounds according to the acquired movement type and determining the current adjustment amount for the collected ambient sounds according to the acquired movement amount comprises:

determining, based on a preset correspondence between movement types and adjustment types, the current adjustment type according to the determined movement type, and acquiring the current adjustment amount for the collected ambient sounds according to a preset correspondence between movement amounts and adjustment amounts.

3. The method according to claim 1, wherein in a case where the movement behavior of the adjuster includes a first movement type corresponding to a noise reduction adjustment and a second movement type corresponding to a monitoring adjustment, the step of determining the current adjustment type for the collected ambient sounds according to the acquired movement type and determining the current adjustment amount for the collected ambient sounds according to the acquired movement amount comprises:

when monitoring that the movement behavior of the adjuster is the first movement type, determining the current adjustment type for the collected ambient sounds to be a first adjustment type for the noise reduction adjustment and determining a current noise reduction amount for the collected ambient sounds according to the acquired movement amount; and, when monitoring that the movement behavior of the adjuster is the second movement type, determining the current adjustment type for the collected ambient sounds to be a second adjustment type for the monitoring adjustment and determining a current amplification amount for the collected ambient sounds according to the acquired movement amount.

4. The method according to claim 3, wherein the step of monitoring the movement behavior of the adjuster in real time and acquiring the movement amount and the movement type of the adjuster if the adjuster moves comprises:

in a case where the adjuster is implemented as a rotatable component or a pushbutton, setting a demarcation point on a movement track of the adjuster, determining the movement type of the adjuster to be the first movement type when detecting that the adjuster moves towards a preset side of the demarcation point whereas determining the movement type of the adjuster to be the second movement type when detecting that the adjuster moves towards the other side of the demarcation point, and acquiring the movement amount based on a displacement of the adjuster relative to the demarcation point;

in a case where the adjuster is implemented as a first key and a second key, determining the movement type of the adjuster to be the first movement type when monitoring that the first key is pressed whereas determining the movement type of the adjuster to be the second movement type when monitoring that the second key is pressed, and acquiring the movement amount based on times the first or the second key is pressed.

5. The method according to claim 1, wherein the step of determining the adjustment type and the adjustment amount for the collected ambient sounds comprises:

receiving, from an earphone application client installed on a terminal, the adjustment type and the adjustment amount for the collected ambient sounds, wherein the adjustment type for the collected ambient sounds includes a first adjustment type corresponding to a noise reduction adjustment and a second adjustment type corresponding to a monitoring adjustment.

6. The method according to claim 5, further comprising:

monitoring, in real time, whether or not a mandatory monitoring mode triggering condition is met and, when monitoring that the mandatory monitoring mode triggering condition is met, recording a current playing volume and the current adjustment amount of ambient sounds and adjusting the collected ambient sounds by the adjustment amount of ambient sounds preset for a mandatory monitoring mode or adjusting the collected ambient sounds by the adjustment amount of ambient sounds preset for the mandatory monitoring mode and adjusting the playing volume of the earphone to a playing volume preset for the mandatory monitoring mode, whereas when monitoring that the mandatory monitoring mode triggering condition is not met, adjusting the earphone according to the recorded playing volume and the recorded adjustment amount of ambient sounds to the former working state.

7. The method according to claim 6, wherein the mandatory monitoring mode triggering condition is whether a command received from the earphone application client installed on the terminal is a command of entering the mandatory monitoring mode or a command of exiting the mandatory monitoring mode.

8. The method according to claim 1, further comprising:

monitoring, in real time, whether or not a mandatory monitoring mode triggering condition is met and, when monitoring that the mandatory monitoring mode triggering condition is met, recording a current playing volume and the current adjustment amount of ambient sounds and adjusting the collected ambient sounds by the adjustment amount of ambient sounds preset for a mandatory monitoring mode or adjusting the collected ambient sounds by the adjustment amount of ambient sounds preset for the mandatory monitoring mode and adjusting the playing volume of the earphone to a playing volume preset for the mandatory monitoring mode, whereas when monitoring that the mandatory monitoring mode triggering condition is not met, adjusting the earphone according to the recorded playing volume and the recorded adjustment amount of ambient sounds to the former working state.

9. The method according to claim 8, wherein, the mandatory monitoring mode triggering condition is whether a mandatory monitoring mode triggering button is pressed.

10. An earphone, comprising: at least one microphone arranged on an external side of the earphone to collect ambient sounds, characterized in that the earphone further comprises:

an adjusting device which is adapted for a user to adjust the collected ambient sounds as needed;

a main control chip which is configured to monitor an adjustment of the adjusting device and determine an adjustment type and an adjustment amount for the collected ambient sounds according to the adjustment of the adjusting device; and further comprises a processor and a memory storing program instructions, which, when executed by the processor, cause the processor to perform steps comprising:

carrying out a noise reduction adjustment and/or monitoring adjustment for the collected ambient sounds by the determined adjustment amount according to the determined adjustment type;

wherein the adjusting device is a mechanically movable adjuster which is arranged on a housing of the earphone or on a housing of a wire controller of the earphone;

the adjuster is provided with an electrical port which connects with the processor; the processor is electronically connected with or integrated in the main control chip;

the main control chip monitors a movement behavior of the adjuster in real time, and acquires a movement amount and a movement type of the adjuster if the adjuster moves; and the main control chip determines a current adjustment type for the collected ambient sounds according to the acquired movement type and determines a current adjustment amount for the collected ambient sounds according to the acquired movement amount.

11. The earphone according to claim 10, wherein in a case where the adjuster is implemented as a rotatable component, a rotation demarcation point is set on a rotation track of the rotatable component, the main control chip determines the movement type of the rotatable component to be a first movement type when detecting that the rotatable component rotates towards a preset side of the rotation demarcation point, whereas determines the movement type of the rotatable component to be a second movement type when detecting that the rotatable component rotates towards the other side of the rotation demarcation point, and acquires the movement amount based on a rotation amount of the rotatable component relative to the rotation demarcation point;

in a case where the adjuster is implemented as a pushbutton, a route demarcation point is set on a push route of the pushbutton, the main control chip determines the movement type of the adjuster to be the first movement type when detecting that the pushbutton slides towards a preset side of the route demarcation point whereas determines the movement type of the adjuster to be the second movement type when detecting that the pushbutton slides towards the other side of the route demarcation point, and acquires the movement amount based on a distance the pushbutton slides from the route demarcation point; and in a case where the adjuster is implemented as a first key and a second key, the main control chip determines the movement type of the adjuster to be the first movement type when monitoring that the first key is pressed whereas determines the movement type of the adjuster to be the second movement type when monitoring that the second key is pressed, and acquires the movement amount based on times the first or the second key is pressed.

12. The earphone according to claim 10, wherein in a case where the adjusting device is a mechanically movable adjuster arranged on the housing of the earphone or on the housing of the wire controller of the earphone, the adjuster is provided with an electrical port which connects with the processor; the main control chip acquires a movement direction and the movement amount of the adjuster when detecting a movement of the adjuster, wherein the movement amount is the amount of movement of the adjuster from the former position thereof, and the movement type is determined based on a preset correspondence between movement directions and movement types; the main control chip also determines, based on a preset correspondence between movement types and adjustment types, the adjustment type according to the determined movement type, and calculates the adjustment amount for the collected ambient sounds according to a preset correspondence between movement amounts and adjustment amounts.

13. The earphone according to claim 10, wherein the processor is further configured to be capable of executing the stored program instructions to to receive a triggering by the user, wherein the main control chip is also configured to monitor, in real time, an output from the processor, determine whether or not a triggering condition is met according to the output from the processor, and when the triggering condition is met, record a current playing volume and the current adjustment amount of ambient sounds and adjust the collected ambient sounds by an adjustment amount of ambient sounds preset or adjust the collected ambient sounds by an adjustment amount of ambient sounds preset and adjust the playing volume of the earphone to a playing volume preset, when the triggering condition is not met, adjust the earphone according to the recorded playing volume and the recorded adjustment amount of ambient sounds to the former working state.

14. An earphone, comprising:

at least one microphone arranged on an external side of the earphone to collect ambient sounds;

a receiving device which is adapted to receive, from an earphone application client installed on a terminal, an adjustment type and an adjustment amount for the collected ambient sounds, wherein the adjustment type for the collected ambient sounds includes a first adjustment type for a noise reduction adjustment and a second adjustment type for a monitoring adjustment;

a main control chip configured to determine the received adjustment type and the received adjustment amount; and further comprising a processor and a memory storing program instructions, which, when executed by the processor, cause the processor to perform steps comprising:

carrying out the noise reduction adjustment and/or the monitoring adjustment for the collected ambient sounds by the determined adjustment amount according to the determined adjustment type;

wherein the receiving device is provided with an electrical port which connects with the processor: the processor is electronically connected with or integrated in the main control chip;

the main control chip determines a current adjustment type for the collected ambient sounds according to the received adjustment type and determines a current adjustment amount for the collected ambient sounds according to the received adjustment amount.

15. A terminal, comprising:

an earphone application client which is installed on the terminal to provide, on an interface thereof, a first virtual adjuster that can be touched to set an adjustment type and an adjustment amount for ambient sounds and a second virtual adjuster that can be touched to set a playing volume, wherein the adjustment type for ambient sounds includes a first adjustment type corresponding to a noise reduction adjustment and a second adjustment type corresponding to a monitoring adjustment; and a transmitting device configured to transmit the set adjustment type and the set adjustment amount for ambient sounds, as well as the set playing volume to the earphone;

wherein the step of setting the adjustment type and the adjustment amount for the ambient sounds comprises:

monitoring a movement behavior of the first virtual adjuster in real time and acquiring a movement amount and a movement type of the first virtual adjuster if the first virtual adjuster moves;

setting a current adjustment type for the collected ambient sounds according to the acquired movement type and setting a current adjustment amount for the collected ambient sounds according to the acquired movement amount.

16. A method of adjusting ambient sounds for an earphone, wherein the earphone collects ambient sounds using at least one external microphone, and the method comprises:

determining an adjustment type and an adjustment amount for the collected ambient sounds; and adjusting, according to the determined adjustment type, the collected ambient sounds by the determined adjustment amount;

wherein a touchpad with a multi-point touch control function is arranged on a housing of the earphone, the touchpad is electronically connected with a main control chip of the earphone, and a noise reduction module and/or a monitoring module are/is electronically connected with or integrated in the main control chip; and the step of determining the adjustment type and the adjustment amount for the collected ambient sounds comprises:

detecting a movement track and a movement direction of a finger of a user on the touchpad;

determining the adjustment amount for the collected ambient sounds according to the detected movement track; and determining, based on a preset correspondence between movement directions and adjustment types, the adjustment type according to the detected movement direction, wherein the adjustment type for the ambient sounds collected includes a first adjustment type corresponding to a noise reduction adjustment and a second adjustment type corresponding to a monitoring adjustment.

17. The method according to claim 16, further comprising:

monitoring, in real time, whether or not a mandatory monitoring mode triggering condition is met and, when monitoring that the mandatory monitoring mode triggering condition is met, recording a current playing volume and the current adjustment amount of ambient sounds and adjusting the collected ambient sounds by the adjustment amount of ambient sounds preset for a mandatory monitoring mode or adjusting the collected ambient sounds by the adjustment amount of ambient sounds preset for the mandatory monitoring mode and adjusting the playing volume of the earphone to a playing volume preset for the mandatory monitoring mode, whereas when monitoring that the mandatory monitoring mode triggering condition is not met, adjusting the earphone according to the recorded playing volume and the recorded adjustment amount of ambient sounds to the former working state.

18. The method according to claim 17, wherein the mandatory monitoring mode triggering condition is whether the touchpad is covered by a palm of the user.

19. An earphone, comprising: at least one microphone arranged on an external side of the earphone to collect ambient sounds, characterized in that the earphone further comprises:

an adjusting device which is adapted for a user to adjust the collected ambient sounds as needed;

a main control chip which is configured to monitor an adjustment of the adjusting device and determine an adjustment type and an adjustment amount for the collected ambient sounds according to the adjustment of the adjusting device; and further comprising a processor and a memory storing program instructions, which, when executed by the processor, cause the processor to perform steps comprising:

carrying out a noise reduction adjustment and/or a monitoring adjustment for the collected ambient sounds by the determined adjustment amount according to the determined adjustment type;

wherein a touchpad with a multi-point touch control function is arranged on a housing of the earphone, the touchpad is electronically connected with the main control chip of the earphone, and the noise reduction module and/or the monitoring module are/is electronically connected with or integrated in the main control chip; and the step of determining the adjustment type and the adjustment amount for the collected ambient sounds comprises:

detecting a movement track and a movement direction of a finger of the user on the touchpad;

determining the adjustment amount for the collected ambient sounds according to the detected movement track; and determining, based on a preset correspondence between movement directions and adjustment types, the adjustment type according to the detected movement direction, wherein the adjustment type for the ambient sounds collected includes a first adjustment type corresponding to the noise reduction adjustment and a second adjustment type corresponding to the monitoring adjustment.

20. The earphone according to claim 19, wherein in a case where the adjusting device is the touchpad with the multi-point touch control function which is arranged on the housing of the earphone, the touchpad is electronically connected with the main control chip of the earphone to detect the movement track and the movement direction of the finger of the user on the touchpad; the main control chip also determines the adjustment amount for the collected ambient sounds according to the detected movement track and determines, based on the preset correspondence between movement directions and adjustment types, the adjustment type according to the detected movement direction.

* * * * *